(12) United States Patent
Zhang

(10) Patent No.: US 9,382,204 B2
(45) Date of Patent: Jul. 5, 2016

(54) INHIBITORS TARGETING THE DNA-BINDING DOMAIN OF HUMAN STAT3 FOR TREATMENT OF METASTATIC CANCERS

(71) Applicant: Jian-Ting Zhang, Carmel, IN (US)

(72) Inventor: Jian-Ting Zhang, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/496,384

(22) Filed: Sep. 25, 2014

(65) Prior Publication Data

US 2015/0094353 A1    Apr. 2, 2015

Related U.S. Application Data

(60) Provisional application No. 61/883,814, filed on Sep. 27, 2013, provisional application No. 61/923,902, filed on Jan. 6, 2014.

(51) Int. Cl.
    C07D 207/44    (2006.01)
(52) U.S. Cl.
    CPC .................................. C07D 207/44 (2013.01)
(58) Field of Classification Search
    CPC ................................................... C07D 207/44
    See application file for complete search history.

(56) References Cited

U.S. PATENT DOCUMENTS

2010/0041685 A1* 2/2010 Tweardy ................ A61K 31/19
                                                               514/274
2011/0319362 A1* 12/2011 Wang ..................... A61K 31/41
                                                               514/80

OTHER PUBLICATIONS

Ito N, Tamano S, Shirai T. A medium-term ratliver bioassay for rapid in vivo detection of carcinogenic potential of chemicals. Cancer Sci. Jan. 2003;94(1):3-8.*
Bowman, et al., STATs in Oncogenesis, Oncogene, 2000, 19:2474-2488.
Bromberg, et al., Stat3 as an Oncogene, Cell, 1999, 98:295-303.
Bromberg, et al., The Role of STATs in Transcriptional Control and Their Impact on Cellular Function, Oncogene, 2000, 19:2468-2473.
Cheng, et al., Twist Is Transcriptionally Induced by Activation of STAT3 and Mediates STAT3 Oncogenic Function, Journal of Biological Chemistry, 2008, 283(21):14665-14673.
Darnell, Jr., et al., Jak-STAT Pathways and Transcriptional Activation in Response to IFNs and Other Extracellular Signaling Proteins, Science, 1994, 264:1415-1421.
Debnath, et al., Small Molecular Inhibitors of Signal Transducer and Activator of Transcription 3 (Stat3) Protein, Journal of Medicinal Chemistry, 2012, 55:6645-6668.
Diaz, et al., Activation of Stat3 in Primary Tumors from High-Risk Breast Cancer Patients is Associated with Elevated Levels of Activated Src and Survivin Expression, Clinical Cancer Research, 2006, 12(1):20-28.
Dolled-Filhart, et al., Tissue Microarray Analysis of Signal Transducers and Activators of Transcription 3 (Stat3) and Phospho-Stat3 (Tyr705) in Node-negative Breast Cancer Shows Nuclear Localization Is Associated with a Better Prognosis, Clinical Cancer Research, 2003, 9:594-600.
Fletcher, et al., Disruption of Transcriptionally Active Stat3 Dimers With Non-Phosphorylated, Salicylic Acid-Based Small Molecules: Potent in Vitro and Tumor Cell Activities, Chembiochem, 2009, 10(12):1959-1964.
Garcia, et al., Constitutive Activation of Stat3 in Fibroblasts Transformed by Diverse Oncoproteins and in Breast Carcinoma Cells, Cell Growth & Differentiation, 1997, 8:1267-1276.
Graves, et al., Rescoring Docking Hit Lists for Model Cavity Sites: Predictions and Experimental Testing, J. Mol. Biol., 2008, 377:914-934.
Hirano, et al., Roles of STAT3 in Mediating the Cell Growth, Differentiation and Survival Signals Relayed Through the IL-6 Family of Cytokine Receptors, Oncogene, 2000, 19:2548-2556.
Huang, et al., A Small Molecule Compound Targeting STAT3 DNA-Binding Domain Inhibits Cancer Cell Proliferation, Migration, and Invasion, ACS Chemical Biology, 2014, 9:1188-1196.
Hughes, et al., Principles of Early Drug Discovery, British Journal of Pharmacology, 2011, 162:1239-1249.
Itoh, et al., Requirement of STAT3 Activation for Maximal Collagenase-1 (MMP-1) Induction by Epidermal Growth Factor and Malignant Characteristics in T24 Bladder Cancer Cells, Oncogene, 2006, 25:1195-1204.
Lang, et al., DOCK 6: Combining Techniques to Model RNA-small Molecular Complexes, RNA, 2009, 15:1219-1230.
Lee, et al., STAT3: A Target to Enhance Antitumor Immune Response, Current Topics in Microbiology and Immunology, 2011, 344:41-59.
Li, et al., Activation of the Signal Transducers and Activators of the Transcription 3 Pathway in Alveolar Epithelial Cells Induces Inflammation and Adenocarcinomas in Mouse Lung, Cancer Research, 2007, 67(18):8494-8503.
Lin, et al., A Novel Small Molecule, LLL12, Inhibits STAT3 Phosphorylation and Activities and Exhibits Potent Growth-Suppressive Activity in Human Cancer Cells, Neoplasia, 2010, 12(1):39-50.
Lin, et al., Novel STAT3 Phosphorylation Inhibitors Exhibit Potent Growth-Suppressive Activity in Pancreatic and Breast Cancer Cells, Cancer Research, 2010, 70(6):2445-2454.
Liu, H., et al., A New Mechanism of Drug Resistance in Breast Cancer Cells: Fatty Acid Synthase Overexpression-Mediated Palmitate Overproduction, Mol. Cancer Ther, 2008, 7(2):263-270.

(Continued)

*Primary Examiner* — Paul Zarek
(74) *Attorney, Agent, or Firm* — Quarles & Brady LLP

(57) ABSTRACT

The present invention provides STAT3 inhibitors which preferentially suppress proliferation of cancer over non-cancer cells and inhibit migration and invasion of malignant cells. The inhibitors of the present invention selectively inhibit STAT3 binding to DNA without affecting the activation and dimerization of STAT3. Furthermore, the inhibitors of the present invention inhibit expression of STAT3 downstream target genes and STAT3 binding to chromatin in situ.

4 Claims, 23 Drawing Sheets
(6 of 23 Drawing Sheet(s) Filed in Color)

(56) References Cited

OTHER PUBLICATIONS

Liu, J., et al., Critical Residue That Promotes Protein Dimerization: A Story of Partially Exposed Phe25 in 14-3-3o, J. Chem. Inf. Model., 2011, 51(10):2612-2625.

Liu, Y., et al., Expression Profiling of ABC Transporters in a Drug-Resistant Breast Cancer Cell Line Using AmpArray, Molecular Pharmacology, 2005, 68(2):430-438.

Liu, Z., et al., Regulation of Expression by Promoters Versus Internal Ribosome Entry Site in the 5'-untranslated Sequence of the Human Cyclin-dependent Kinase Inhibitor p27kip1, Nucleic Acids Research, 2005, 33(12):3763-3771.

Mantel, et al., Mouse Hematopoietic Cell-Targeted STAT3 Deletion: Stem/Progenitor Cell Defects, Mitochondrial Dysfunction, ROS Overproduction, and a Rapid Aging-Like Phenotype, Blood, 2012, 120(13):2589-2599.

Mendez, et al., Chromatin Association of Human Origin Recognition Complex, Cdc6, and Minichromosome Maintenance Proteins During the Cell Cycle: Assembly of Prereplication Complexes in Late Mitosis, Molecular and Cellular Biology, 2000, 20(22):8602-8612.

Meng, et al., Automated Docking with Grid-Based Energy Evaluation, Journal of Computational Chemistry, 1992, 13 (4):505-524.

Nkansah, et al., Observation of Unphosphorylated STAT3 Core Protein Binding to Target dsDNA by PEMSA and X-ray Crystallography, FEBS Letters, 2013, 587:833-839.

Onufriev, et al., Modification of the Generalized Born Model Suitable for Macromolecules, J. Phys. Chem. B, 2000, 104:3712-3720.

Pettersen, et al., UCSF Chimera—A Visualization System for Exploratory Research and Analysis, Journal of Computational Chemistry, 2004, 25:1605-1612.

Ren, et al., Identification of a High-Affinity Phosphopeptide Inhibitor of Stat3, Bioorganic & Medicinal Chemistry Letters, 2003, 13:633-636.

Schust, et al., Staltic: A Small-Molecule Inhibitor of STAT3 Activation and Dimerization, Chemistry & Biology, 2006, 13:1235-1242.

Sehgal, et al., Requirement for Matrix Metalloproteinase-9 (Gelatinase B) Expression in Metastasis by Murine Prostate Carcinoma, American Journal of Pathology, 1998, 152(2):591-596.

Sen, et al., First-in-Human Trial of a STAT3 Decoy Oligonucleotide in Head and Neck Tumors: Implications for Cancer Therapy, Cancer Discovery, 2012, 2:694-705.

Siddiquee, et al., Selective Chemical Probe Inhibitor of Stat3, Identified Through Structure-Based Virtual Screening, Induces Antitumor Activity, PNAS, 2007, 104(18):7391-7396.

Song, H., et al., A Low-Molecular-Weight Compound Discovered Through Virtual Database Screening Inhibits Stat3 Function in Breast Cancer Cells, PNAS, 2005, 102(13):4700-4705.

Song, L., et al., Activation of Stat3 by Receptor Tyrosine Kinases and Cytokines Regulates Survival in Human Non-Small Cell Carcinoma Cells, Oncogene, 2003, 22:4150-4165.

Timofeeva, et al., Mechanisms of Unphosphorylated STAT3 Transcription Factor Binding to DNA, Journal of Biological Chemistry, 2012, 287(17):14192-14200.

Turkson, et al., Phosphotyrosyl Peptides Block Stat3-Mediated DNA Binding Activity, Gene Regulation, and Cell Transformation, Journal of Biological Chemistry, 2001, 276(48):45443-45455.

Turkson, et al., Novel Peptidomimetic Inhibitors of Signal Transducer and Activator of Transcription 3 Dimerization and Biological Activity, Molecular Cancer Therapeutics, 2004, 3(3):261-269.

Wei, et al., Stat3 Activation Regulates the Expression of Vascular Endothelial Growth Factor and Human Pancreatic Cancer Angiogenesis and Metastasis, Oncogene, 2003, 22:319-329.

Welte, et al., STAT3 Deletion During Hematopoiesis Causes Crohn's Disease-Like Pathogenesis and Lethality: A Critical Role of STAT3 in Innate Immunity, PNAS, 2003, 100(4):1879-1884.

Xie, et al., Stat3 Activation Regulates the Expression of Matrix Metalloproteinase-2 and Tumor Invasion and Metastasis, Oncogene, 2004, 23:3550-3560.

Yang, et al., Unphosphorylated STAT3 Accumulates in Response to IL-6 and Activates Transcription by Binding to NFKB, Genes & Development, 2007, 21:1396-1408.

Yue, et al., Targeting STAT3 in Cancer: How Successful Are We?, Expert Opin. Investig. Drugs, 2009, 18(1):45-56.

Zhang, et al., IL-6 Regulates MMP-10 Expression Via JAK2/STAT3 Signaling Pathway in a Human Lung Adenocarcinoma Cell Line, Anticancer Research, 2009, 29:4497-4502.

Zhang, et al., Orally Bioavailable Small-Molecule Inhibitor of Transcription Factor Stat3 Regresses Human Breast and Lung Cancer Xenografts, PNAS, 2012, 109(24):9623-9628.

Berg, Inhibition of Transcription Factors with Small Organic Molecules, Current Opinion in Chemical Biology, 2008, 12(4):464-471.

Brady, et al., Disposition of Biologics, Advances in Pharmacology, 2012, 63:257-277.

Buettner, et al., Alkylation of Cysteine 468 in Stat3 Defines a Novel Site for Therapeutic Development, ACS Chemical Biology, 2011, 6(5):432-443.

Caboni, et al., Beyond the Ligand-Binding Pocket: Targeting Alternate Sites in Nuclear Receptors, Medicinal Research Reviews, 2013, 33(5):1081-1118.

Chen, et al., STAT3: A Critical Transcription Activator in Angiogenesis, Medicinal Research Reviews, 2008, 28 (2):185-200.

Chiarle, et al., Stat3 is Required for ALK-Mediated Lymphomagenesis and Provides a Possible Therapeutic Target, Nature Medicine, 2005, 11:623-629.

Choi, et al., Prognostic Significance of p-STAT3 in Patients with Bulky Cervical Carcinoma Undergoing Neoadjuvant Chemotherapy, Journal of Obstetrics and Gynaecology Research, 2010, 36(2):304-310.

Costantino, et al., STAT3 as a Target for Cancer Drug Discovery, Current Medicinal Chemistry, 2008, 15 (9):834-843.

Deng, et al., Small Molecule Inhibitors of Stat3 Signaling Pathway, Current Cancer Drug Targets, 2007, 7(1):91-107.

Devarajan, et al., STAT3 as a Central Regulator of Tumor Metastases, Current Molecular Medicine, 2009, 9 (5):626-633.

Frye, The Art of the Chemical Probe, Nature Chemical Biology, 2010, 6(3):159-161.

Hao, et al., Discovery of the Catechol Structural Moiety as a Stat3 SH2 Domain Inhibitor by Virtual Screening, Bioorganic & Medicinal Chemistry Letters, 2008, 18(18):4988-4992.

Leung, et al., DNA-Binding Small Molecules as Inhibitors of Transcription Factors, Medicinal Research Reviews, 2013, 33(4):823-846.

Schust, et al., A High-Throughput Fluorescence Polarization Assay for Signal Transducer and Activator of Transcription 3, Analytical Biochemistry, 2004, 330(1):114-118.

Siddiquee, et al., An Oxazole-Based Small-Molecule Stat3 Inhibitor Modulates Stat3 Stability and Processing and Induces Antitumor Cell Effects, ACS Chemical Biology, 2007, 2(12):787-798.

Zhong, et al., Stat3: A STAT Family Member Activated by Tyrosine Phosphorylation in Response to Epidermal Growth Factor and Interleukin-6, Science, 1994, 264(5155):95-98.

\* cited by examiner

_US 9,382,204 B2_

SEQUENCE LISTING

<160> NUMBER OF SEQ ID NOS: 24

<210> SEQ ID NO 1
<211> LENGTH: 24
<212> TYPE: DNA
<213> ORGANISM: Artificial Sequence
<220> FEATURE:
<223> OTHER INFORMATION: cold SIE probe

<400> SEQUENCE: 1
agcttcattt cccgtaaatc ccta                                          24

<210> SEQ ID NO 2
<211> LENGTH: 24
<212> TYPE: DNA
<213> ORGANISM: Artificial Sequence
<220> FEATURE:
<223> OTHER INFORMATION: COLD SIE probe

<400> SEQUENCE: 2
agcttcattt cccgtaaatc ccta                                          24

<210> SEQ ID NO 3
<211> LENGTH: 18
<212> TYPE: DNA
<213> ORGANISM: Artificial Sequence
<220> FEATURE:
<223> OTHER INFORMATION: Primers for real-time PCR; STAT3; forward

<400> SEQUENCE: 3
ggcccctcgt catcaaga                                                 18

<210> SEQ ID NO 4
<211> LENGTH: 24
<212> TYPE: DNA
<213> ORGANISM: Artificial Sequence
<220> FEATURE:
<223> OTHER INFORMATION: Primers for real-time PCR; STAT3; reverse

<400> SEQUENCE: 4
tttgaccagc aacctgactt tagt                                          24

<210> SEQ ID NO 5
<211> LENGTH: 20
<212> TYPE: DNA
<213> ORGANISM: Artificial Sequence
<220> FEATURE:
<223> OTHER INFORMATION: Primers for real-time PCR; CyclinD1; forward

<400> SEQUENCE: 5
cttcctctcc aaaatgccag                                               20

```
<210> SEQ ID NO 6
<211> LENGTH: 20
<212> TYPE: DNA
<213> ORGANISM: Artificial Sequence
<220> FEATURE:
<223> OTHER INFORMATION: Primers for real-time PCR; CyclinD1; reverse

<400> SEQUENCE: 6
agagatggaa gggggaaaga                                               20

<210> SEQ ID NO 7
<211> LENGTH: 17
<212> TYPE: DNA
<213> ORGANISM: Artificial Sequence
<220> FEATURE:
<223> OTHER INFORMATION: Primers for real-time PCR; Survivin; forward

<400> SEQUENCE: 7
tgcctggcag ccctttc                                                  17

<210> SEQ ID NO 8
<211> LENGTH: 20
<212> TYPE: DNA
<213> ORGANISM: Artificial Sequence
<220> FEATURE:
<223> OTHER INFORMATION: Primers for real-time PCR; Survivin; reverse

<400> SEQUENCE: 8
cctccaagaa gggccagttc                                               20

<210> SEQ ID NO 9
<211> LENGTH: 20
<212> TYPE: DNA
<213> ORGANISM: Artificial Sequence
<220> FEATURE:
<223> OTHER INFORMATION: Primers for real-time PCR; VEGF; forward

<400> SEQUENCE: 9
tacctccacc atgccaagtg                                               20

<210> SEQ ID NO 10
<211> LENGTH: 21
<212> TYPE: DNA
<213> ORGANISM: Artificial Sequence
<220> FEATURE:
<223> OTHER INFORMATION: Primers for real-time PCR; VEGF; reverse

<400> SEQUENCE: 10
gatgattctg ccctcctcct t                                             21

<210> SEQ ID NO 11
<211> LENGTH: 24
<212> TYPE: DNA
<213> ORGANISM: Artificial Sequence
<220> FEATURE:
<223> OTHER INFORMATION: Primers for real-time PCR; MMP-1; forward

<400> SEQUENCE: 11
agctagctca ggatgacatt gatg                                          24

<210> SEQ ID NO 12
<211> LENGTH: 17
<212> TYPE: DNA
<213> ORGANISM: Artificial Sequence
<220> FEATURE:
<223> OTHER INFORMATION: Primers for real-time PCR; MMP-1; reverse
```

-continued

<400> SEQUENCE: 12
gccgatgggc tggacag                                                    17

<210> SEQ ID NO 13
<211> LENGTH: 21
<212> TYPE: DNA
<213> ORGANISM: Artificial Sequence
<220> FEATURE:
<223> OTHER INFORMATION: Primers for real-time PCR; MMP-2; forward

<400> SEQUENCE: 13
tagcatgtcc ctaccgagtc t                                               21

<210> SEQ ID NO 14
<211> LENGTH: 19
<212> TYPE: DNA
<213> ORGANISM: Artificial Sequence
<220> FEATURE:
<223> OTHER INFORMATION: Primers for real-time PCR; MMP-2; reverse

<400> SEQUENCE: 14
attggatggc agtagctgc                                                  19

<210> SEQ ID NO 15
<211> LENGTH: 18
<212> TYPE: DNA
<213> ORGANISM: Artificial Sequence
<220> FEATURE:
<223> OTHER INFORMATION: Primers for real-time PCR; MMP-9; forward

<400> SEQUENCE: 15
tgacagcgac aagaagtg                                                   18

<210> SEQ ID NO 16
<211> LENGTH: 19
<212> TYPE: DNA
<213> ORGANISM: Artificial Sequence
<220> FEATURE:
<223> OTHER INFORMATION: Primers for real-time PCR; MMP-9; reverse

<400> SEQUENCE: 16
cagtgaagcg gtacatagg                                                  19

<210> SEQ ID NO 17
<211> LENGTH: 20
<212> TYPE: DNA
<213> ORGANISM: Artificial Sequence
<220> FEATURE:
<223> OTHER INFORMATION: Primers for real-time PCR; MMP-10; forward

<400> SEQUENCE: 17
atccaagagg catccatacc                                                 20

<210> SEQ ID NO 18
<211> LENGTH: 20
<212> TYPE: DNA
<213> ORGANISM: Artificial Sequence
<220> FEATURE:
<223> OTHER INFORMATION: Primers for real-time PCR; MMP-10; reverse

<400> SEQUENCE: 18
tcaaccttag gctcaactcc                                                 20

<210> SEQ ID NO 19
<211> LENGTH: 18

```
<212> TYPE: DNA
<213> ORGANISM: Artificial Sequence
<220> FEATURE:
<223> OTHER INFORMATION: Primers for real-time PCR; Twist; forward

<400> SEQUENCE: 19
cgggagtccg cagtctta                                                  18

<210> SEQ ID NO 20
<211> LENGTH: 20
<212> TYPE: DNA
<213> ORGANISM: Artificial Sequence
<220> FEATURE:
<223> OTHER INFORMATION: Primers for real-time PCR; Twist; reverse

<400> SEQUENCE: 20
tgaatcttgc tcagcttgtc                                                20

<210> SEQ ID NO 21
<211> LENGTH: 23
<212> TYPE: DNA
<213> ORGANISM: Artificial Sequence
<220> FEATURE:
<223> OTHER INFORMATION: Primers for real-time PCR; GAPDH; forward

<400> SEQUENCE: 21
aaggactcat gaccacagtc cat                                            23

<210> SEQ ID NO 22
<211> LENGTH: 19
<212> TYPE: DNA
<213> ORGANISM: Artificial Sequence
<220> FEATURE:
<223> OTHER INFORMATION: Primers for real-time PCR; GAPDH; reverse

<400> SEQUENCE: 22
ccatcacgcc acagtttcc                                                 19

<210> SEQ ID NO 23
<211> LENGTH: 20
<212> TYPE: DNA
<213> ORGANISM: Artificial Sequence
<220> FEATURE:
<223> OTHER INFORMATION: The primer for PCR of cyclinD1 promoter;
      forward

<400> SEQUENCE: 23
aacttgcaca ggggttgtgt                                                20

<210> SEQ ID NO 24
<211> LENGTH: 23
<212> TYPE: DNA
<213> ORGANISM: Artificial Sequence
<220> FEATURE:
<223> OTHER INFORMATION: The primer for PCR of cyclin D1 promoter;
      reverse

<400> SEQUENCE: 24
gagaccacga aagggggtga ctg                                            23
```

INHIBITORS TARGETING THE DNA-BINDING DOMAIN OF HUMAN STAT3 FOR TREATMENT OF METASTATIC CANCERS

CROSS-REFERENCE TO RELATED APPLICATIONS

This application claims priority to U.S. Provisional Application No. 61/883,814, filed Sep. 27, 2013, and U.S. Provisional Application No. 61/923,902, filed Jan. 30, 2014, both of which are incorporated by reference for all purposes.

STATEMENT REGARDING FEDERALLY SPONSORED RESEARCH OR DEVELOPMENT

Not Applicable.

BACKGROUND OF THE INVENTION

STAT3 (Signal Transducers and Activators of Transcription 3), a member of the Janus kinase (JAK)/STAT signaling pathway, is a central transcription factor activated by phosphorylation of a conserved tyrosine residue (Tyr$^{705}$) in response to extracellular cytokines and growth factors. Once activated, STAT3 dimerizes and translocates into nucleus to induce transcription of downstream target genes. Overexpression and/or constitutive activation of STAT3 has been detected in a number of human malignancies including lung and breast cancers. Subcutaneous injection of cells harboring constitutively-activated STAT3 (STAT3c) resulted in tumor formation. STAT3c overexpression in mouse alveolar type II epithelial cells led to lung inflammation and consequently spontaneous lung bronchoalveolar adenocarcinoma. Furthermore, inhibiting STAT3 expression using antisense oligonucleotides significantly impaired the growth of human and mouse nucleophosmin-anaplastic lymphoma kinase tumors in xenograft models. Thus, STAT3 is an attractive target for anticancer drug discovery.

Various inhibitors of STAT3 have been identified in the past, including peptidomimetics and small molecule compounds designed from the peptidomimetics or via high-throughput and virtual screening. Some of these inhibitors suppressed tumor growth in vivo, but none have moved into clinical testing. The common feature of all these inhibitors is that they are designed to inhibit the binding of SH2 domain to pTyr$^{705}$ residue for activation or to inhibit phosphorylation of Tyr$^{705}$. This approach is problematic because unphosphorylated STAT3 can bind to DNA and may still be functional. Thus, disrupting the interactions between SH2 domain and pTyr$^{705}$ of STAT3 or STAT3 activation alone may not completely inhibit STAT3.

Interestingly, targeting the DNA-binding domain (DBD) of STAT3 has not been in the main stream of research, possibly because DBS is generally considered "undruggable" with flat and similar surface areas that may not allow appropriate and selective binding by small molecules. Nevertheless, a decoy oligonucleotide targeting the DBD of STAT3 is currently in clinical testing for human head and neck cancers.

Thus, inhibiting STAT3 promises an attracting strategy for treatment of advanced and metastatic cancers.

SUMMARY OF THE INVENTION

The present invention provides STAT3 inhibitors which preferentially suppress proliferation of cancer over non-cancer cells and inhibit migration and invasion of malignant cells. The inhibitors of the present invention selectively inhibit STAT3 binding to DNA without affecting the activation and dimerization of STAT3. Furthermore, the inhibitors of the present invention inhibit expression of STAT3 downstream target genes and STAT3 binding to chromatin in situ.

In one embodiment, the present invention provides a pharmaceutical composition comprising (a) a pharmaceutically effective amount of an inhibitor of signal transducer and activator of transcription 3 (STAT3), or its pharmaceutically acceptable salt or a solvate thereof, and (b) a pharmaceutically suitable carrier. The inhibitors of the present invention target the DNA binding domain of STAT3. A suitable compound can be identified by measuring the inhibition of the DNA-binding activity of STAT3. In some embodiments, a suitable compound inhibits the DNA-binding activity of STAT3 in a dose-dependent manner with an IC50 no greater than 50 µM, 40 µM, 30 µM, or preferably 20 µM measured by electrophoretic mobility shift assay (EMSA). In some embodiments, the inhibitors of the present invention include, but are not limited to, the compounds of Table 3.

In one embodiment, the inhibitor comprises 4-[(3E)-3-[(4-nitrophenyl)-methylidene]-2-oxo-5-phenylpyrrol-1-yl]benzoic acid (inS3-54). In other embodiments, the inhibitors of the present invention comprise analogues of inS3-54. In still other embodiments, the inhibitors of the present invention comprise the structure

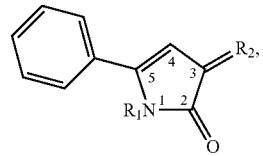

where R1 is selected from the group consisting of

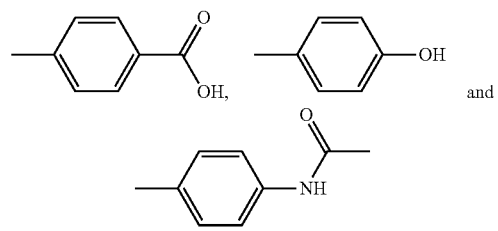

and R2 is selected from the group consisting of

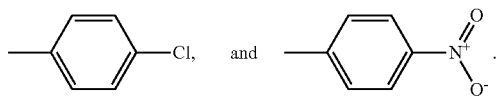

In one embodiment, the inhibitor comprises the structure

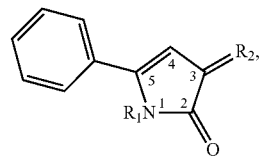

wherein R1 is

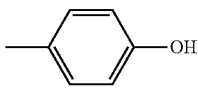

and R2 is

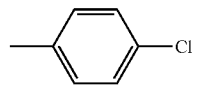

(A18).

In another embodiment, the inhibitor comprises the structure

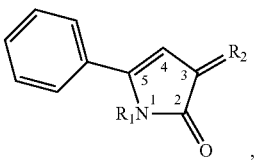

wherein R1 is

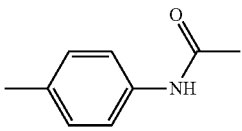

and R2 is

(A26).

In another embodiment, the inhibitor comprises the structure

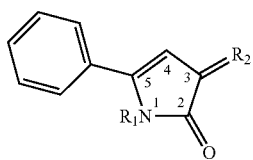

wherein R1 is

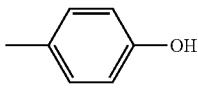

and R2 is

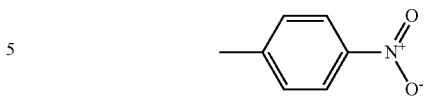

(A69).

In another embodiment, the present invention provides methods of treating cancer comprising the step of administering to a subject in need thereof a therapeutically effective amount of a composition comprising the inhibitors of the present invention.

DESCRIPTION OF THE FIGURES

The patent or application file contains at least one drawing executed in color. Copies of this patent or patent application publication with color drawings will be provided by the Office upon request and payment of the necessary fee.

DETAILED DESCRIPTION OF THE INVENTION

In General

Figure 1:
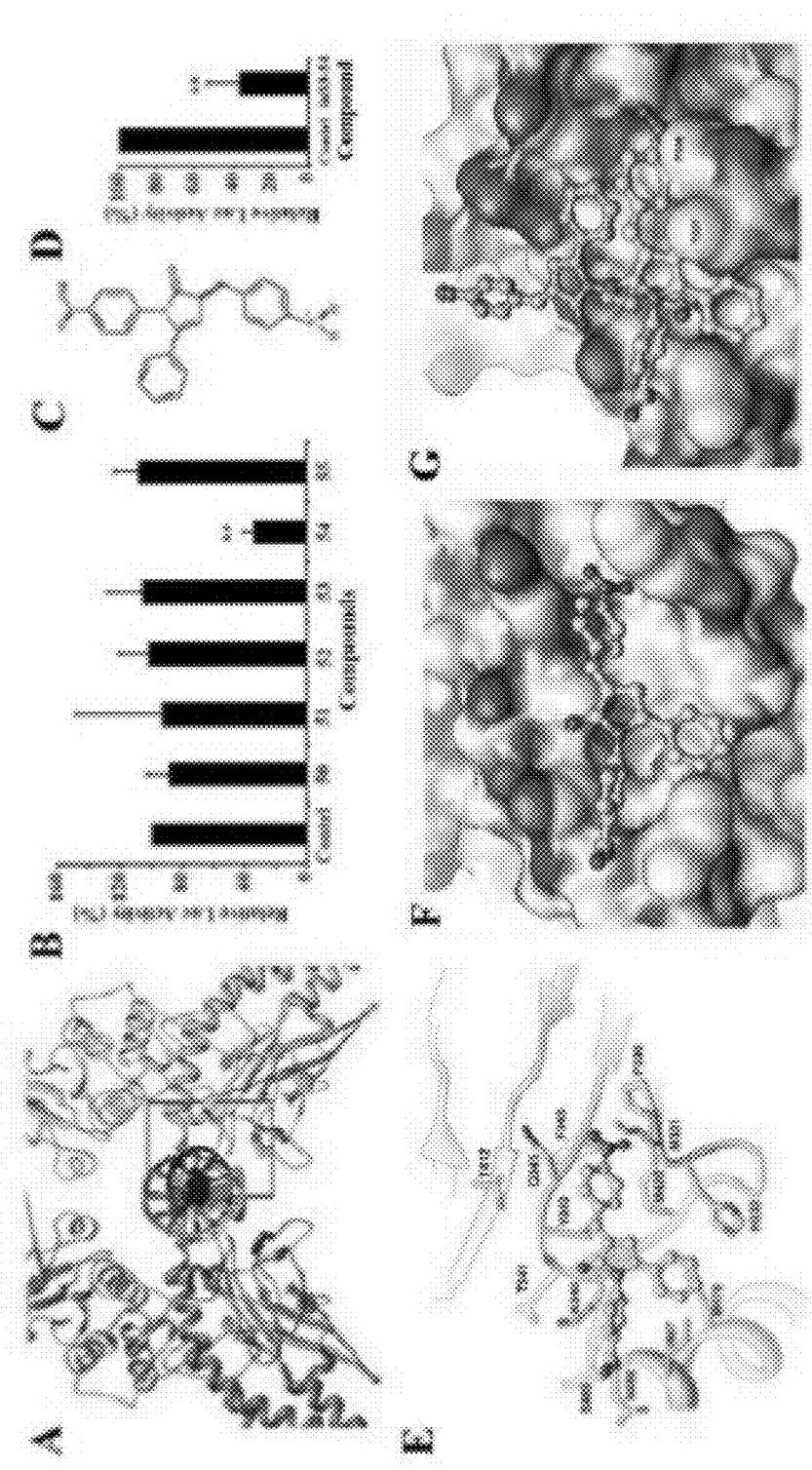
FIG. 1. Schematic diagram and identification of inS3-54 by virtual screening. (A) DNA-STAT3 complex structure (PDB code: 1BG1). The red box shows the site for docking in one of the STAT3 subunit. (B) Luciferase activity assay of MDA-MB-231 cells stably transfected with STAT3-dependent luciferase reporter. (C) Structure of inS3-54. (D) Luciferase activity assay of H1299 cells transiently transfected with STAT3-dependent luciferase reporter. (E) Simulated average complex structure of inS3-54 in the DBD of STAT3. (F & G) Molecular surface of STAT3 (F) and STAT1 (G) complexed with inS3-54 from MD simulation with orientation shown in gold for STAT3 and pink for STAT1. Molecular surface is colored with gray for carbon, blue for nitrogen, red for oxygen and yellow for sulfur. (**p<0.01).

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The Invention.

The present invention provides STAT3 inhibitors which preferentially suppress proliferation of cancer over non-cancer cells and inhibit migration and invasion of malignant cells. The inhibitors of the present invention selectively inhibit STAT3 binding to DNA without affecting the activation and dimerization of STAT3. Furthermore, the inhibitors of the present invention inhibit expression of STAT3 downstream target genes and STAT3 binding to chromatin in situ.

In one embodiment, the present invention provides a pharmaceutical composition comprising (a) a pharmaceutically effective amount of an inhibitor of signal transducer and activator of transcription 3 (STAT3), or its pharmaceutically acceptable salt or a solvate thereof, and (b) a pharmaceutically suitable carrier. By "pharmaceutically effective amount" we mean any amount effective to, for example, kill cancer cells, reduce or maintain tumor size, inhibit tumor growth or metastasis rate, and the like.

In one embodiment, the inhibitors of the present invention target the DNA binding domain of STAT3. A suitable compound can be identified by measuring the inhibition of the DNA-binding activity of STAT3.

In some embodiments, a suitable compound inhibits the DNA-binding activity of STAT3 in a dose-dependent manner with an IC50 no greater than 50 µM, 40 µM, 30 µM, or preferably 20 µM measured by electrophoretic mobility shift assay (EMSA).

In some embodiments, the inhibitors of the present invention include, but are not limited to, the inhibitors shown in Table 3.

In one embodiment, the inhibitor comprises 4-[(3E)-3-[(4-nitrophenyl)-methylidene]-2-oxo-5-phenylpyrrol-1-yl]benzoic acid (inS3-54).

In other embodiments, the inhibitors of the present invention comprise analogues of inS3-54.

In still other embodiments, the inhibitors of the present invention comprise the structure

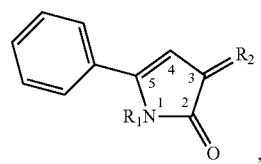

where $R_1$ is selected from the group consisting of

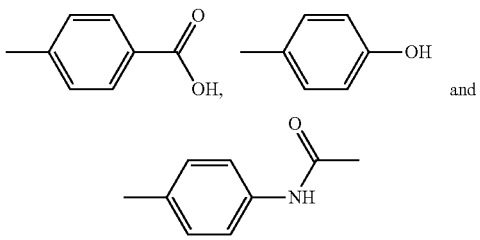

and $R_2$ is selected from the group consisting of

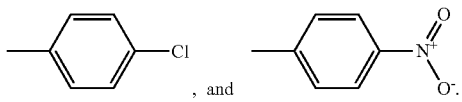

In one embodiment, the inhibitor comprises the structure

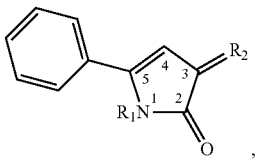

wherein $R_1$ is

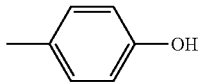

and $R_2$ is

(A18).

In another embodiment, the inhibitor comprises the structure

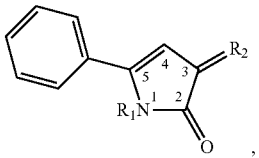

wherein $R_1$ is

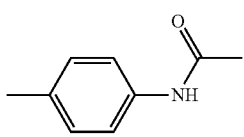

and $R_2$ is

(A26).

In another embodiment, the inhibitor comprises the structure

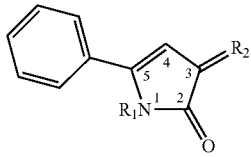

wherein $R_1$ is

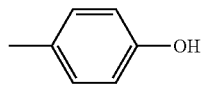

and $R_2$ is

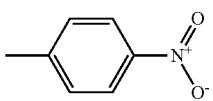

(A69).

In another embodiment, the present invention provides methods of treating cancer comprising the step of administering to a subject in need thereof a therapeutically effective amount of a composition comprising the inhibitors of the present invention.

By "subject" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

By "subject in need thereof" we mean an animal or human subject who is at risk of having cancer [e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness]. Additionally or alternatively, the subject in need thereof can be a healthy human subject undergoing a routine well-being check up.

By "administering" or "administration" includes any means for introducing the STAT3 inhibitors into the subject, preferably into the systemic circulation. Examples include but are not limited to oral, buccal, sublingual, pulmonary, transdermal, transmucosal, as well as subcutaneous, intraperitoneal, intravenous, and intramuscular injection. Any dosage effective to treat cancer is suitable for this invention. In one embodiment, the dosage ranges from about 0.001 μg to 10 μg per day per kg bodyweight. In other embodiments, the effective dosage ranges from about 0.0005 ug to 5 ug per day per kg bodyweight. In still other embodiments, the effective dosage ranges from about 0.1 ug to 5 g per day per kg bodyweight.

By "therapeutically effective amount' or "pharmaceutically effective amount", we mean an amount of the STAT3 inhibitor that, when administered to a subject for treating a disease, is sufficient to effect the desired treatment for the disease. By "effective" we mean effective to for example, prevent the onset of the symptoms or complications, alleviate symptoms or complications, or eliminate the disease, condition, or disorder. An "effective" amount will prevent, alleviate, maintain or ameliorats any of the primary phenomena (initiation, progression, metastasis) or secondary symptoms associated with the disease. For example, effective treatment may kill diseased cells or reduce tumor size, inhibit tumor growth or metastasis, decrease tumor growth rate or metastasis rate, or maintain tumor size or the development of metastasis. The "therapeutically effective" or pharmaceutically effective" amount will vary depending on the compound, the disease state being treated, the severity or the disease treated, the age and relative health of the subject, the route and form of administration, the judgment of the attending medical practitioner, and other factors.

By "treating" or "treatment", we mean the management and care of a patient for the purpose of combating the disease, condition, or disorder. The terms embrace both preventative, i.e., prophylactic, and palliative treatment. Treating includes the administration of a compound of the present invention to prevent the onset of the symptoms or complications, alleviating the symptoms or complications, or eliminating the disease, condition, or disorder. Treatment also prevents, alleviates, maintains or ameliorates any of the primary phenomena (initiation, progression, metastasis) or secondary symptoms associated with the disease. For example, the treatment may kill diseased cells or reduce tumor size, inhibit tumor growth or metastasis, decrease tumor growth rate or metastasis rate, or maintain tumor size or the development of metastasis.

A compound is administered to a patient in a therapeutically effective amount. A compound can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. It is also noted that the dose of the compound can be varied over time. A compound can be administered using an immediate release formulation, a controlled release formulation, or combinations thereof. The term "controlled release" includes sustained release, delayed release, and combinations thereof.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description of the novel compounds and methods of the present invention are to be regarded as illustrative in nature and not restrictive.

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Identification of a STAT3 Inhibitor Targeting its DBD

To identify compounds that can directly block the interaction between STAT3 and its DNA substrate, we first examined the crystal structure of STAT3β-complexed with DNA and performed virtual docking of approximately 200,000 compounds to the DBD (FIG. 1A). Top-scoring compounds with phosphate groups functioning similar as phosphates in DNA were eliminated due to their potential inability to permeate into cells. The remaining 1000 top-scoring compounds were then docked onto the DBD of STAT1 to eliminate compounds that also bind to STAT1. The final list was shortened to 100 potentially specific candidates.

Figure 2:
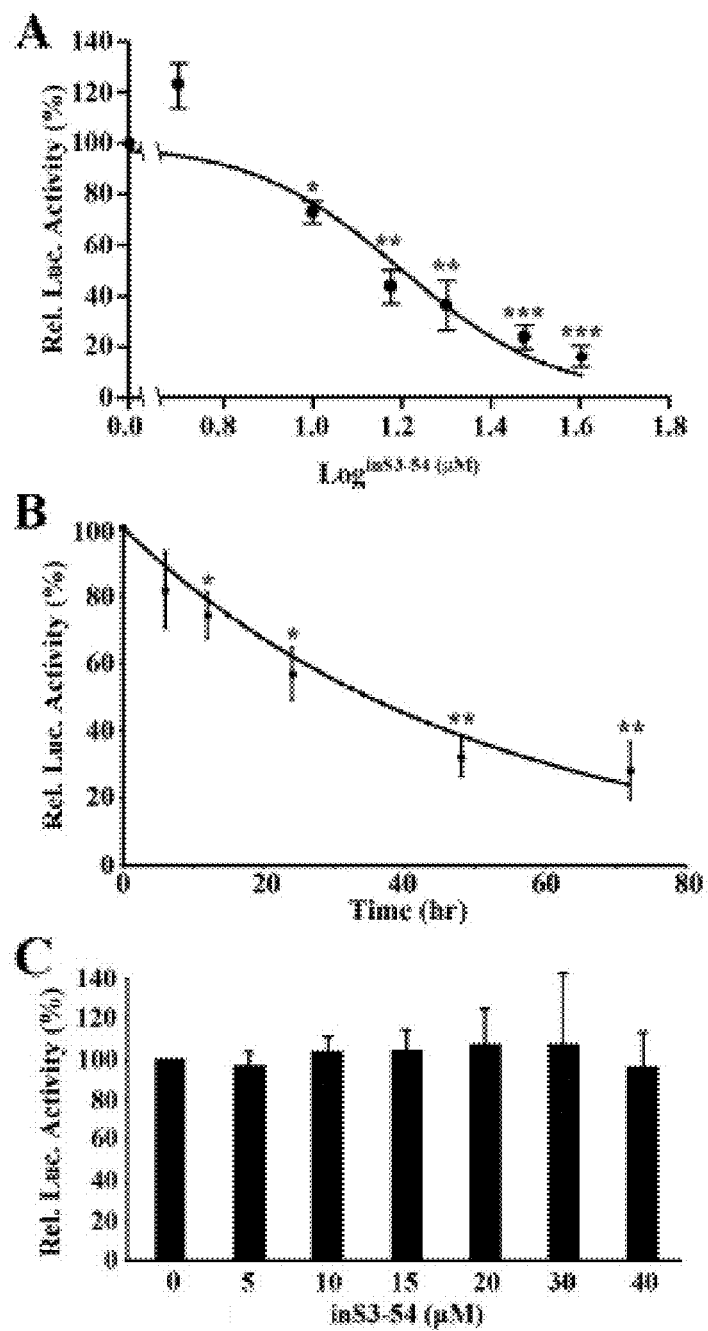
FIG. 2. Effect of inS3-54 on STAT3-dependent and independent luciferase reporter expression. (A and B). Effect on STAT3-dependent luciferase reporter expression. MDA-MB-231-STAT3 cells harboring a STAT3-dependent luciferase reporter construct were treated with increasing concentration of inS3-54 for 72 hrs (A) or with 20 μM inS3-54 for various time (B) followed by luciferase reporter assay. (C). Effect on STAT3-independent luciferase expression. H1299 cells were transiently transfected with a luciferase reporter construct driven by a p27 promoter lacking STAT3-binding sequence followed by treatment with different concentrations of inS3-54 for 48 hrs. (*P<0.05, P<0.01, *P<0.001).

Of the 100 virtual compounds, 57 chemical samples were obtained and tested for their ability to inhibit STAT3-dependent luciferase reporter expression in MDA-MB-231 cells. One of the compounds, #54, exhibited significant inhibitory activity (FIG. 1B) in a dose- and timedependent manner (FIG. 2A-2B) with an IC50 of 13.8±0.4 μM and the time required for 50% inhibition at 29.2±4.7 hours. This compound, 4-[(3E)-3-[(4-nitrophenyl)-methylidene]-2-oxo-5-phenylpyrrol-1-yl]benzoic acid (FIG. 1C), was named inS3-54 and used to search the PubChem database for high-throughput screening data on STAT3 inhibitors. No compound with the same structure was found.

To confirm the activity of the compound using re-supplied material, to eliminate the potential issues associated with the use of a single stable clone harboring the luciferase reporter gene, and to test if inS3-54 is cell line specific, we tested newly synthesized inS3-54 using H1299 cells transiently transfected with the STAT3-driven luciferase reporter plasmid. FIG. 1D shows that the newly synthesized inS3-54 significantly inhibits STAT3-dependent luciferase reporter expression. Thus, the activity of inS3-54 is not derived from potential contamination in the original supply and it is not dependent on cell line specific or transfection method used.

Furthermore, inS3-54 did not inhibit the reporter expression driven by a p27 promoter containing no STAT3-binding site (FIG. 2C), suggesting that inS3-54 inhibition of reporter expression is unlikely due to its non-specific effect on the reporter gene. Together, these observations suggest that inS3-54 is a good chemical probe.

InS3-54 Selectively Inhibits the DNA-Binding Activity of STAT3.

To determine the selectivity of inS3-54 for STAT3 over STAT1, we first performed molecular dynamics (MD) simulation and generalized born surface area (GBSA) analyses for the binding free energy (ΔGbind) of inS3-54 docked in the DBD of these proteins. Table 1 shows that both STAT molecules have favorable electrostatic (ΔEele) and van der Waals (ΔEvdw) interaction energy although they are more favorable for STAT3 than STAT1.

TABLE 1 inS3-54 binding free energies and energy components in STAT1 and STAT3

| | $\Delta E_{solute}$ (kcal/mol) ± SE | | $\Delta G_{solv}$ (kcal/mol) ± SE | | | |
|---|---|---|---|---|---|---|
| | $\Delta E_{ele}$ | $\Delta E_{vdw}$ | $\Delta G_{es}$ | $\Delta G_{nes}$ | $\Delta E_{tot\_ele}$(kcal/mol) ± SE | $\Delta G_{bind}$ (kcal/mol) ± SE |
| STAT1 | −139.6 ± 3.4 | −23.1 ± 1.0 | 149.6 ± 2.4 | −4.0 ± 0.1 | 10.1 ± 0.4 | −17.1 ± 1.0 |
| STAT3 | −144.3 ± 4.4 | −27.5 ± 0.9 | 148.0 ± 2.8 | −4.6 ± 0.1 | 3.6 ± 0.8 | −28.4 ± 0.9 |

The energy from solvation (ΔGsolv) reverses these favorable energies for both proteins. However, the reversal effect is less for STAT3 than for STAT1. Consequently, the total ΔGbind is much more favorable for STAT3 (−28.4 kcal/mol) than STAT1 (−17.1 kcal/mol). Considering the omitted entropy term, which is always unfavorable, inS3-54 may not bind to STAT1 at all or have a very low affinity.

Examination of the average simulated structures (FIG. 1E) of inS3-54-bound STAT3 and STAT1 agrees with the calculated ΔGbind. Contribution of hydrophobic interactions from STAT3 to inS3-54 binding is mostly from residues Met331, Val343, Met420, Ile467, and Met470. The amino groups of Lys340 and Asn466 stabilize the carboxyl group of inS3-54 by favorable electrostatic interactions. However, the orientation of inS3-54 docked in STAT1 (FIG. 1G) is very different (FIG. 1F). This binding mode in STAT1 likely results in an unfavorable ΔGbind. Forcing inS3-54 to adopt the same orientation in STAT1 as in STAT3 results in clashes between inS3-54 and residues Pro326 and Thr327 of STAT1 (FIG. 1G). Thus, inS3-54 unlikely can bind to STAT1.

Figure 3:
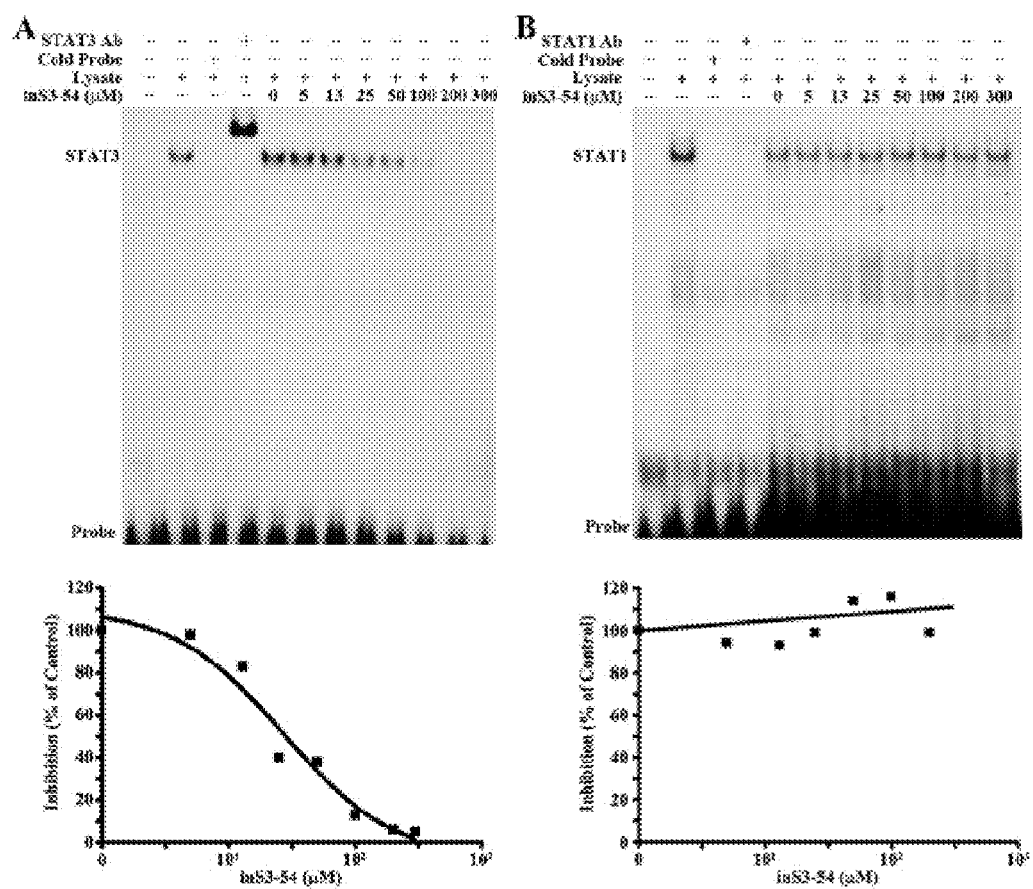
FIG. 3. InS3-54 inhibits the DNA-binding activity of STAT3 but not STAT1. The effect of inS3-54 on the DNA binding activity of STAT3 (A) and STAT1 (B) was determined using EMSA in the absence or presence of excess unlabeled (cold) probe as competitor, antibody for super shift/interference of binding, or different concentrations of inS3-54.

To verify the above findings and to determine the inS3-54 inhibition of the DNA-binding activity of STAT3 or STAT1, we performed electrophoretic mobility shift assay (EMSA) using a [32P]-labeled double strand DNA probe and H1299 cells transiently transfected with FLAGSTAT3 or STAT1. As shown in FIG. 3A, the specific binding of DNA probe to STAT3 was demonstrated using super-shift and competition analyses. InS3-54 inhibited the DNA-binding activity of STAT3 in a dose-dependent manner with an IC50 of ~20 μM, which is consistent with the cell-based reporter assay (see above). The specific binding of DNA probe to STAT1 as shown by interference of binding using STAT1 antibody and competition analyses, however, was not affected by inS3-54 up to 300 μM (FIG. 3B). Thus, inS3-54 selectively inhibits the DNA-binding activity of STAT3 over STAT1.

Binding of inS3-54 to STAT3.

Figure 4:
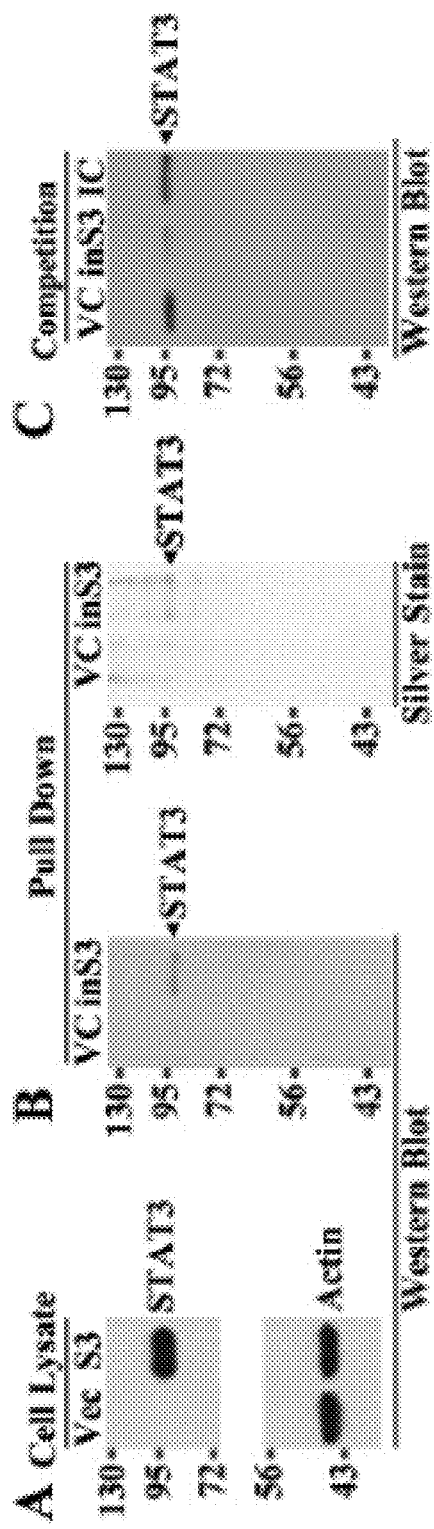
FIG. 4. Binding of inS3-54 to STAT3. (A) Western blot analysis of STAT3 from total lysate of NIH1299 cells transfected with vector (Vec) control or FLAG-STAT3 (S3) cDNA. (B) Pull-down assay of STAT3 from lysate of FLAG-STAT3-transfected H1299 cells using EAHSepharose 4B-conjugated without (vehicle control, VC) or with inS3-54 (inS3). Pull-down materials were separated using SDS-PGAE and Western blot analysis probed with STAT3 antibody or stained with silver. (C) Competition of STAT3-binding to inS3-54-conjugated EAHSepharose 4B beads by excess free inS3-54 (inS3), an irrelevant compound (IC) control or vehicle control (VC).

To verify that inS3-54 can bind to STAT3, we took advantage that inS3-54 contains a carboxyl group and conjugated it to EAH Sepharose 4B. InS3-54-conjugated beads were then used to pull down STAT3 from FLAG-STAT3-transfected H1299 cells followed by Western blot analysis or silver staining FIG. 4A shows the expression of FLAG-STAT3. FIG. 4B shows that inS3-54-conjugated beads successfully pull down STAT3 whereas the vehicle control beads do not. Furthermore, pretreatment of the cell lysate using excess free inS3-54, but not vehicle or an irrelevant compound, inhibited the pull-down of STAT3 by inS3-54-conjugated beads (FIG. 4C). Thus, inS3-54 can bind to STAT3.

InS3-54 is not an Alkylating Agent.

Figure 5:
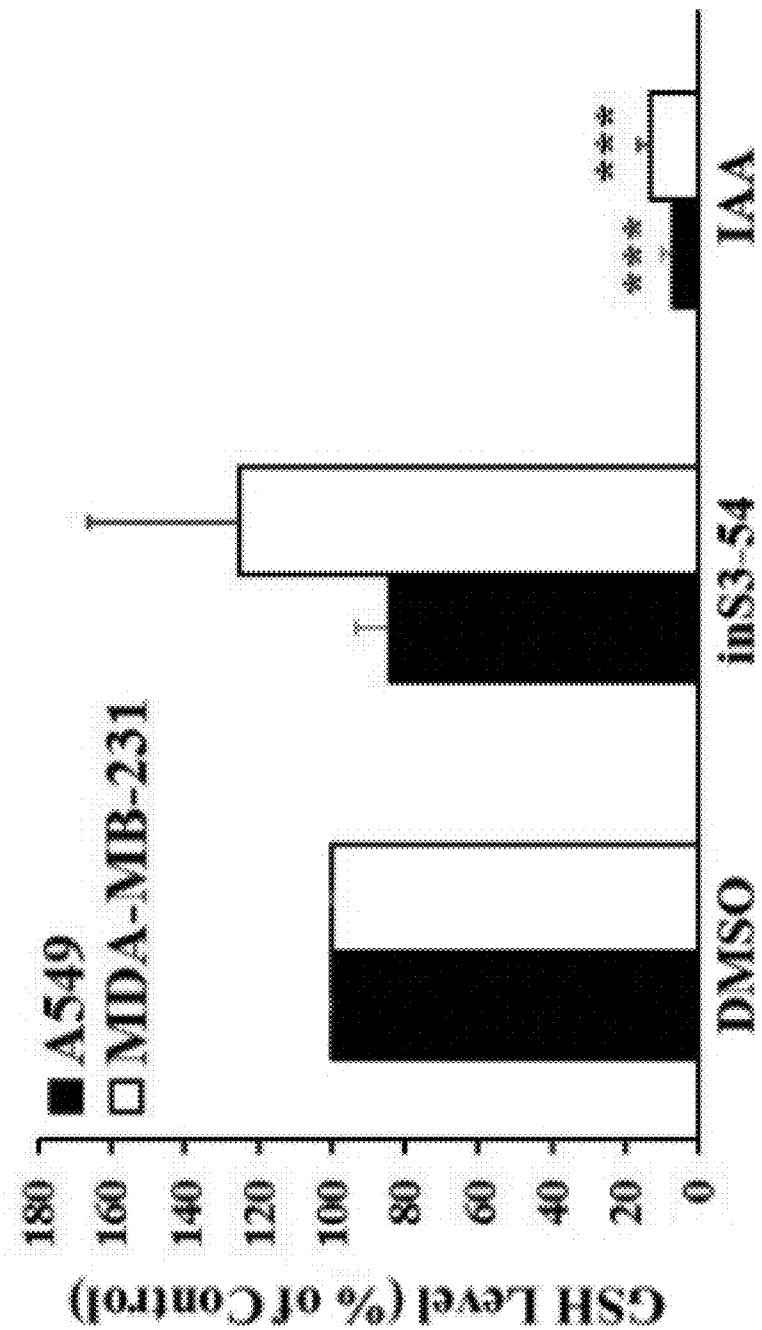
FIG. 5. Effect of inS3-54 glutathione level. A549 and MDA-MB-231 cells were first treated with DMSO or 20 µM inS3-54 for 48 hours or with 15 mM iodoacetamide (IAA) for 30 minutes followed by determination of glutathione level using the GSH-Glo™ glutathione assay kit (Promega, Madison, Wis., USA) per manufacturer's instructions. (***p<0.001).

Recently, it was found that Cys468 in DBD of STAT3 can be alkylated by and covalently linked to a small molecule inhibitor. The finding from pull-down assay (FIG. 4) shows that inS3-54 can bind but not covalently to STAT3, suggesting that inS3-54 did not alkylate STAT3. To further eliminate the possibility that inS3-54 has alkylating activity, we performed luminescence-based glutathione alkylation assay. As shown in FIG. 5, inS3-54 did not significantly reduce glutathione level in both A549 and MDAMB-231 cells. In contrast, the known alkylating agent iodoacetamide significantly reduced the glutathione level. Thus, inS3-54 does not possess any activity to alkylate Cys residues.

InS3-54 does not Inhibit STAT3 Dimerization.

Figure 6:
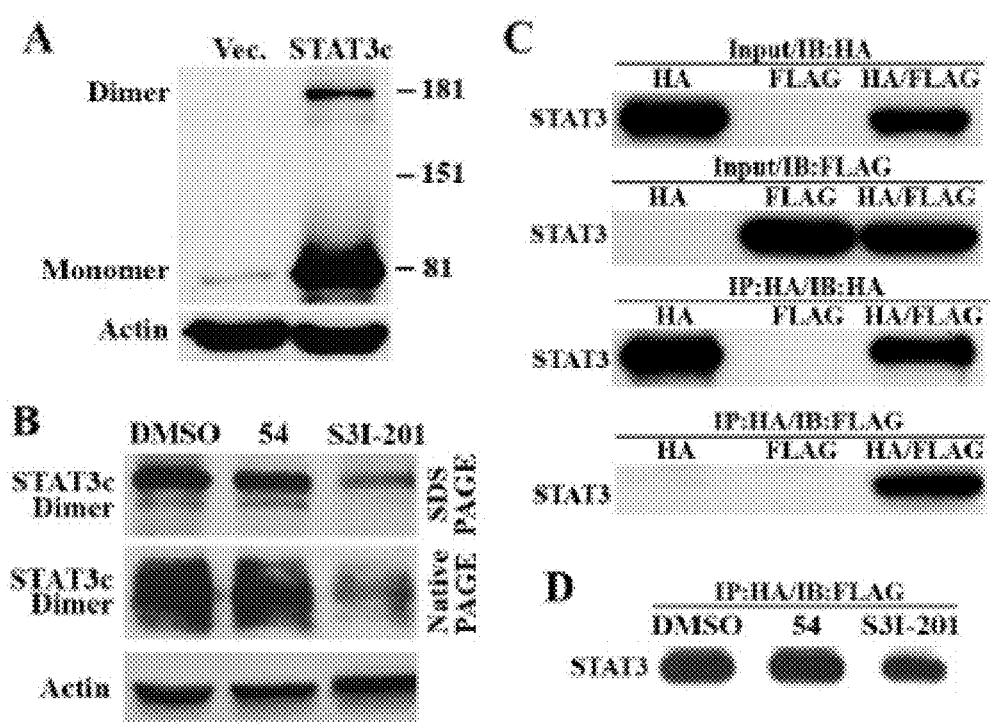
FIG. 6. InS3-54 does not affect STAT3 dimerization. (A) Western blot analysis of STAT3c expression. H1299 cells were transiently transfected with vector control or STAT3c cDNA followed by lysate preparation, separation by non-reducing SDS-PAGE, and Western blot analysis using STAT3 antibody or actin antibody for a loading control. (B) Western blot analysis of STAT3 dimerization. H1299 cells-expressing STAT3c were treated with DMSO vehicle control, 20 µM inS3-54 or S3I-201 for 24 hrs followed by lysate preparation, separation by nonreducing SDS-PAGE or non-denaturing PAGE, and Western blot analysis of STAT3 status. Actin was used as a loading control. (C) Co-expression and immunoprecipitation of HA- and FLAG-tagged STAT3. Lysates from H1299 cells transfected with HA-tagged, FLAG-tagged STAT3, or both were subjected to co-immunoprecipitation using HA antibody and Western blot analyses with HA or FLAG antibodies as we previously described (*J Biol Chem* 279, 9781-19789). (D) Effect of inS3-54 and inS3-54A69 on co-immunoprecipitation. H1299 cells cotransfected with HA- and FLAG-tagged STAT3 were treated with DMSO control, 20 µM inS3-54 or S3I-201 followed by co-immunoprecipitation with HA antibody and Western blot analysis with FLAG antibody.

The SH2 domain of STAT3 has previously been shown to be susceptible for targeting. To eliminate the possibility that inS3-54 works by off-targeting to the SH2 domain, we tested if inS3-54 inhibits STAT3 dimerization using FLAG-STAT3c, which forms spontaneous homo-dimers via formation of intermolecular disulfide bond. FIG. 6A shows that STAT3c is successfully expressed in H1299 cells in both dimeric and monomeric forms separated by non-reducing SDS-PAGE.

However, inS3-54 had no effect on production of dimeric STAT3c separated using non-reducing SDS-PAGE or non-denaturing PAGE (FIG. 6B) while S3I-201, a STAT3 inhibitor that binds to the SH2 domain, inhibited STAT3c dimerization (FIG. 6B). To confirm this observation, we performed a co-immunoprecipitation analysis of HA and FLAG-tagged STAT3. FIG. 6C shows that HA- and FLAG-tagged STAT3 can be coexpressed and co-immunoprecipitated successfully in H1299 cells. inS3-54 had no effect while S3I-201 inhibited the co-immunoprecipitation (indicator of dimerization) between HA- and FLAG-tagged STAT3 (FIG. 6D). Thus, inS3-54 likely does not inhibit STAT3 dimerization or bind to the SH2 domain.

InS3-54 Favorably Inhibits Cancer Cell Survival by Inducing Apoptosis.

Figure 7:
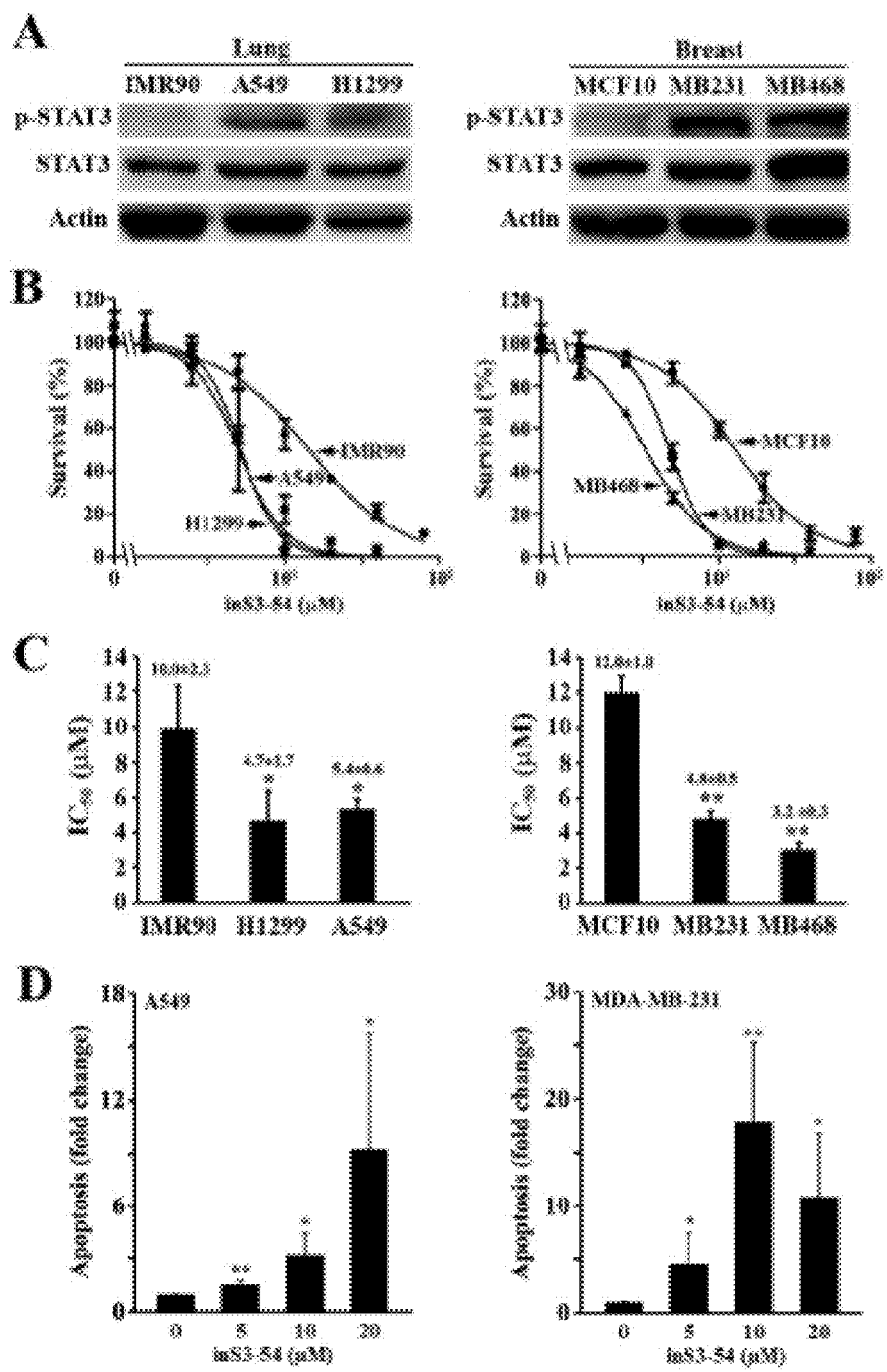
FIG. 7. InS3-54 inhibits cancer cell proliferation. (A) Level of STAT3 expression and activation. Lysates from lung cancer cell lines A549 and H1299 along with a lung fibroblast cell line IMR90 as well as human breast cancer cell lines MDA-MB-231 and MDA-MB-468 along with mammary epithelial cell line MCF10A1 were subjected to Western blot analysis of total and phosphorylated STAT3. Actin was used as a loading control. (B-C) Cytotoxicity assay. IMR90, A549, H1299, MCF10A1, MDA-MB-231, and MDA-MB-468 cell lines were treated with various concentrations of inS3-54 for 72 hrs followed by sulphorhodamine assay. IC50 of inS3-54 for each cell line was derived using PrismPad program. (D) Apoptosis assay. Exponentially growing A549 and MDA-MB-231 cells were treated without or with different concentrations of inS3-54 for 72 hrs followed by determination of apoptosis using ELISA. (**p<0.01; *p<0.05).

Next, we determined whether inS3-54 inhibits growth and survival of cancer cells using two lung cancer cell lines (A549 and H1299) and two breast cancer cell lines (MDA-MB-231 and MDA-MB-468) as well as a normal lung fibroblast (IMR90) and a mammary epithelial cell line (MCF10A1). As shown in FIG. 7A, the cancer cells all had constitutively activated STAT3 as assessed by its phosphorylation status at Tyr705, compared to the normal cells, consistent with previous findings. The cancer cells are also more sensitive to inS3-54 with lower IC50 than the normal cells (3.2-5.4 vs 10-12 μM, see FIGS. 7B-7C), suggesting the existence of a therapeutic window for inS3-54.

To determine if apoptosis contributes to inS3-54 suppression of cancer cell survival, we performed apoptosis analysis of exponentially growing cells using ELISA following inS3-54 treatment for 72 hours. As shown in FIG. 7D, inS3-54 induced apoptosis in both A549 and MDAMB-231 cells in a dose-dependent manner. Treatment with inS3-54 also induced cleavage of PARP in breast cancer cell line MDA-MB-468 (data not shown), a target of activated caspases during execution of apoptosis, confirming that 72-hour treatments with inS3-54 induce apoptosis.

InS3-54 Inhibits Cancer Cell Migration and Invasion.

STAT3 also plays an important role in controlling cell migration and invasion by regulating the expression of genes such as MMP-1, 2, 9, 10, Twist and VEGF important for these cellular processes. To assess the inhibitory effects of inS3-54 on cancer cell migration and invasion, we first performed a wound-healing assay using A549 and MDA-MB-231 cells. FIGS. 8A-8B show that inS3-54 inhibits migration of both A549 and MDA-MB-231 cells in dose- and time-dependent manners. At 24 hours, about 68% and 95% of wounds were healed in the control vehicle-treated A549 and MDA-MB-231 cells, respectively. However, only 54% and 77% of the wounds were healed for these cells at 24 hours following the treatment with 10 µM inS3-54. The wound healing further reduced to 27% and 29% for cells treated with 20 µM inS3-54.

Matrigel invasion assay was then used to determine the effect of inS3-54 on cancer cell invasion. FIGS. 8C-8D show that both A549 and MDA-MB-231 cells exhibit significantly decreased invasion in the presence of inS3-54 compared with DMSO-treated control cells. At 6 hours of treatment with 10 and 20 µM inS3-54, the invasion was reduced to 67% and 49% for A549 cells and to 52% and 24% for MDA-MB-231 cells, respectively, compared with the control treatment groups. At 24 hours of treatment with 10 µM inS3-54, the invasion of A549 and MDA-MB-231 cells was about 71% and 24% of controls, respectively. These numbers were further reduced to 33% and 5% in the presence of 20 µM inS3-54.

Figure 8:
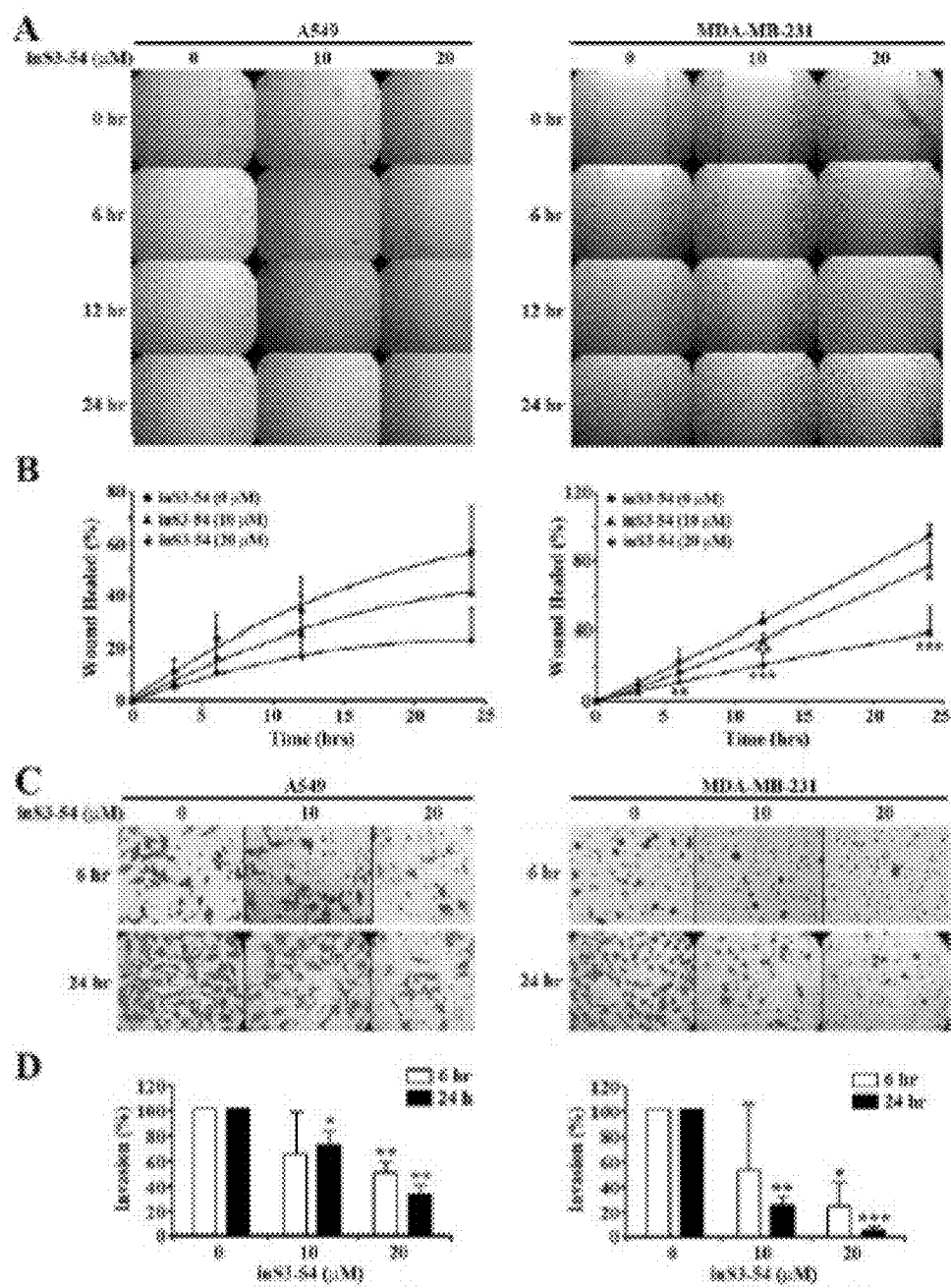
FIG. 8. InS3-54 inhibits cancer cell migration and invasion. (A and B) Effect of inS3-54 on migration. Migration of A549 and MDA-MB-231 cells was assessed by wound healing assay in the presence of 0 (DMSO control), 10 or 20 µM inS3-54. Panel B shows quantification analysis of wound healing assay from triplicate measurements of three independent experiments. (C and D) Effect of inS3-54 on cell invasion. The invasion of A549 and MDA-MB-231 cells were determined in the presence of 0 (DMSO control), 10 or 20 µM inS3-54 for 6 or 24 hrs using Matrigel invasion assay with 10% FBS in the bottom chamber as chemoattractant. Panel D shows quantification of invasion from measurement of 10 random views each of three independent experiments. (*p<0.001; p<0.01; *p<0.05).
Figure 9:
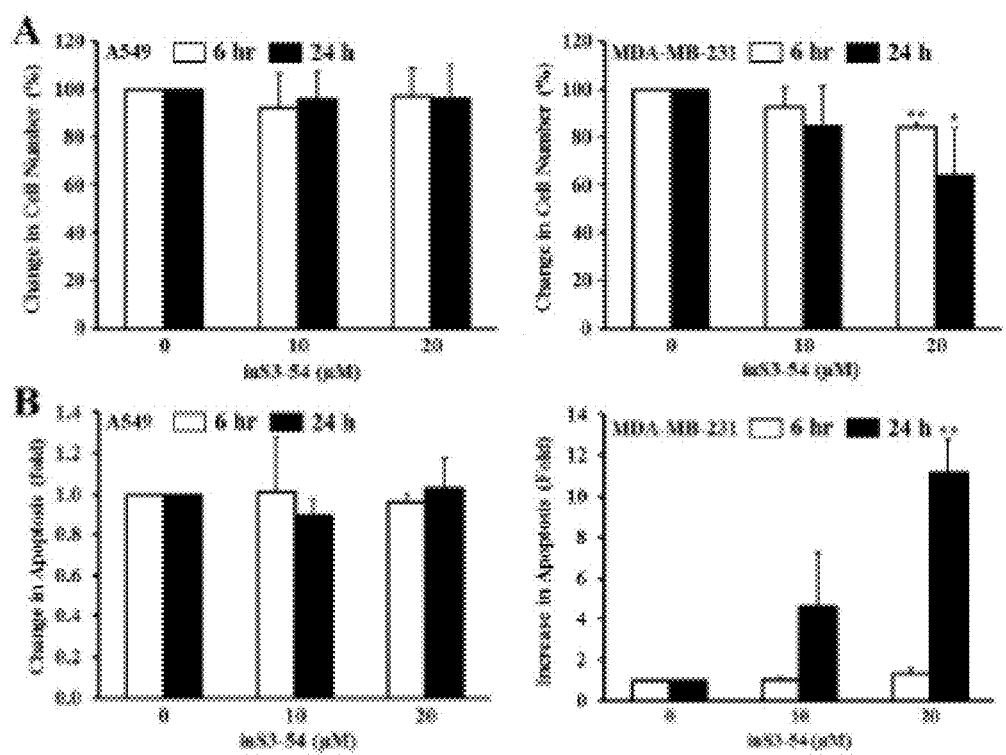
FIG. 9. Effect of inS3-54 on cell growth and apoptosis of confluent cells. 100% confluent A549 and MDA-MB-231 cells were treated with 0 (DMSO vehicle control), 10 or 20 µM inS3-54 for 6 or 24 hrs followed by determination of change in cell number for proliferation (A) or ELISA for apoptosis (B). (**p<0.01; *p<0.05).

Although we used 100% confluent cells and short time incubation in the above assays, inS3-54 inhibition of proliferation may still contribute to the above observed outcome. To eliminate this possibility, we analyzed cell proliferation and apoptosis under the same condition as wound-healing and Matrigel invasion assays with confluent cultures. As shown in supplemental FIG. 9, treatment with 20 µM inS3-54 for 24 hours had no significant effect on proliferation (FIG. 9A) and apoptosis (FIG. 9B) of confluent A549 cells although 20 µM of inS3-54 decreased the proliferation and increases apoptosis of MDA-MB-231 cells compared to the control treatment groups. However, 10 µM inS3-54 did not significantly decrease proliferation or increase apoptosis of MDA-MB-231 cells (FIG. 9), under which condition it significantly reduced the migration and invasion activity of these cells (FIG. 8). Furthermore, no apoptosis was observed at 6 hours of treatment with 20 µM inS3-54. Thus, we conclude that inS3-54 inhibition of migration and invasion is unlikely due to its effect on apoptosis and cell proliferation.

InS3-54 Inhibits the Expression of STAT3 Downstream Target Genes and STAT3 Binding to Genomic DNA.

Figure 10:
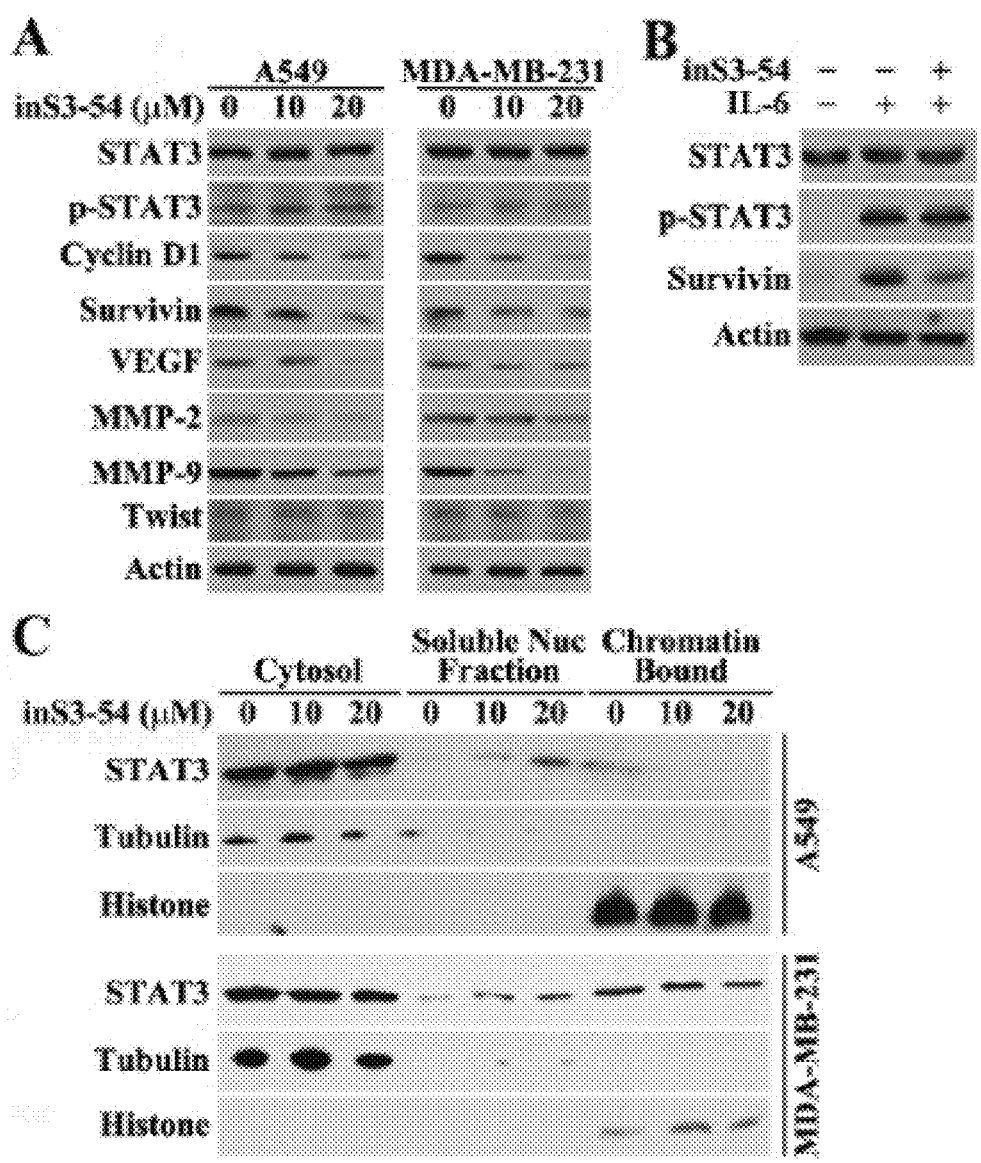
FIG. 10. InS3-54 inhibits the expression of STAT3 downstream target genes and STAT3 binding to chromatin. (A) Effect of inS3-54 on the expression of STAT3 downstream target genes in A549 and MDA-MB-231 cells were treated with 0 (DMSO control), 10 or 20 µM inS3-54 for 48 hrs followed by lysate preparation and Western blot analysis with antibodies indicated. Actin was used as a loading control for Western blot. (B) Inhibition of IL-6 stimulated STAT3 activation. A549 cells were cultured in serum-free medium for 2 days and then were pretreated with 20 µM inS3-54 for 12 hours followed by incubation with 25 ng/ml of IL-6 for 30 minutes. Cells were then harvested and lysed for Western blot analysis of total and phospho-STAT3 and survivin. Actin was used as a loading control. (C) Inhibition of inS3-54 on STAT3 binding to chromatin in-situ. A549 and MDA-MB-231 cells were treated with 0 (DMSO control), 10 or 20 µM inS3-54 for 48 hours followed by fractionation of cytosol, soluble nuclear fraction, and chromatin-bound proteins and Western blot analysis of STAT3 in these fractions.
Figure 11:
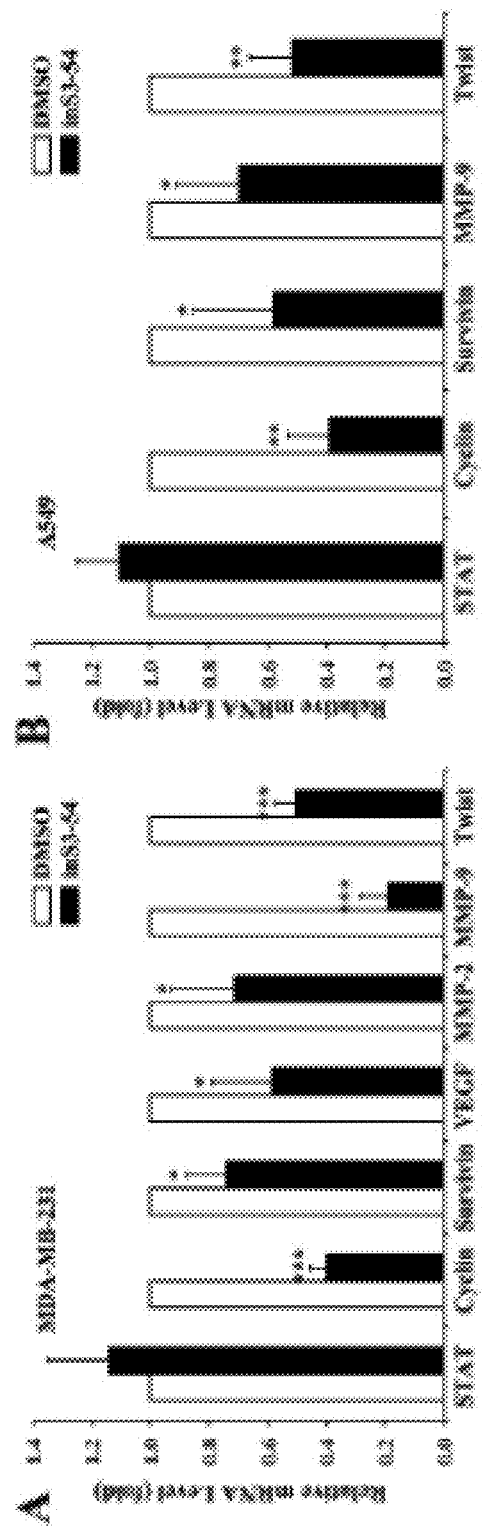
FIG. 11. Effect of inS3-54 on mRNA level of STAT3 downstream target genes. MDA-MB-231 (A) and A549 (B) cells were treated with DMSO control or 20 µM inS3-54 followed by extracting total RNA and real-time PCR analysis. InS3-54 inhibited mRNA level of STAT3 downstream targets in both cells lines. *P<0.05, P<0.01, *P<0.001 significantly different compared with corresponding DMSO-treated control by Student's T-test.

To validate the inhibitory effect of inS3-54 on STAT3 in cells, we next determined the effect of inS3-54 on the expression of known STAT3 downstream target genes. FIG. 10A shows that the expression of cyclin D1, survivin, VEGF, MMP-2, MMP-9, and twist are all decreased following inS3-54 treatment in both A549 and MDA-MB-231 cell lines at protein level. This observation was confirmed by quantitative RT-PCR analysis of mRNAs in both cell lines (FIG. 11).

InS3-54 treatments, however, had no effect on the level of total STAT3 or basal level of Tyr705-phosphorylated STAT3 (FIG. 10A), indicating that inS3-54 does not affect the expression or activation of STAT3. To further determine if inS3-54 possibly inhibits STAT3 activation and phosphorylation, serum-starved A549 cells were pretreated with inS3-54 followed by IL-6 stimulation and Western blot analysis of phosphorylated STAT3. As shown in FIG. 10B, IL-6 stimulated phosphorylation of Tyr705 of STAT3 and expression of the downstream target gene survivin in serum-starved A549 cells, indicating activation of STAT3 by IL-6. Pretreatment with inS3-54 had no effect on IL-6-stimulated phosphorylation of STAT3 but inhibited IL-6 stimulated expression of survivin. Thus, inS3-54 does not affect IL-6 stimulated phosphorylation/activation of STAT3 but inhibits STAT3 transcription activity.

The EMSA data (FIG. 3) show that inS3-54 inhibits the DNA-binding activity of STAT3 in vitro. To further demonstrate that inS3-54 inhibits the DNA-binding activity of STAT3 in situ, we treated A549 and MDA-MB-231 cells with inS3-54 followed by isolation of cytosol, soluble nuclear, and chromatin-bound fractions and determined STAT3 level in these fractions using Western blot. FIG. 10C shows that STAT3 in the chromatin-bound fraction decreases while the STAT3 level in soluble nuclear fraction increases with the increasing concentration of inS3-54, suggesting that inS3-54 effectively inhibits STAT3-binding to its endogenous target sequences on genomic DNA in situ. Taken together with the results shown above, we conclude that inS3-54 specifically inhibits STAT3 activity in binding to endogenous promoters on genomic DNA, resulting in reduced transcription of its downstream target genes.

With the aid of structure-based virtual screening, we successfully identified a human STAT3 inhibitor targeting its DBD, one of the first successful attempts in targeting the prevailing "undruggable" DBD of transcription factors. inS3-54 is selective to STAT3 over STAT1 as demonstrated using EMSA. In-silico analysis shows that inS3-54 could not bind to STAT1 due to physical hindrance from residue Pro326 and Thr327 and, thus, has a much lower affinity to STAT1. The finding that inS3-54 does not inhibit the promoter activity of p27 is also consistent with its selectivity. Finally, the less cytotoxic effect of inS3-54 on normal mammary epithelial and lung fibroblast cells than cancer cells further confirms that inS3-54 is likely selective to STAT3.

As expected, inS3-54 inhibits the DNA-binding activity of STAT3 in both EMSA and cell-based (chromatin binding) assays. Although we have shown that inS3-54 likely binds to STAT3 using pull-down assay, we have not shown if it binds to DBD. However, we have shown that it unlikely binds the SH2 domain. It also does not inhibit STAT3 activation and phosphorylation and does not have alkylating activity. Thus, most likely inS3-54 binds to DBD and directly inhibits the DNA-binding activity of STAT3.

It is noteworthy that inS3-54 has an IC50 of ~20 µM in inhibiting DNA-binding activity in the EMSA assay and an IC50 of ~15.8 µM in luciferase reporter assay. However, the IC50 of inS3-54 in cytotoxicity assay ranges from ~3.2-5.4 µM in cancer to ~10-12 µM in non-cancer cells. Currently, it is unknown why inS3-54 is more effective in inhibiting cell survival than inhibiting DNA binding and luciferase reporter expression. However, because the cytotoxicity assay measures both proliferation and cell death induced by inS3-54, which is an amplified result of reduced expression of STAT3 downstream target genes, the lower IC50 in cytotoxicity assay is likely due to the increased sensitivity of this assay. It may also be possible that inS3-54 has off target effects that can impact on cell survival. However, since inS3-54 does not inhibit STAT1 or transcription factors that drive p27 promoter, this possibility is less likely.

Structure-Based Virtual Screening.

The DNA in the DBD of STAT3β-DNA complex structure (PDB code: 1BG1) was removed and the protein chain was prepared for docking. The DNA-binding groove consisting of residues 329-332, 340-346, 406-412 and 465-468 was chosen as the targeting site for docking (FIG. 1A). Molecular surface was calculated using DMS (Distributed Molecular Surface) program. Partial charges and protons were added to the protein by UCSF Chimera Dock Prep module. In-silico dock screening of 200,000 compounds from the ChemDiv library was performed using UCSF DOCK 6.0 program. The docking of each compound was first scored with the DOCK GRID scoring function. The top-scoring 1000 compounds were analyzed again and re-scored using the AMBER scoring function of DOCK 6.0 package.

The top-scoring compounds were then docked onto the DBD of STAT1 (PDB Code:1BF5) in the same way as to STAT3. Compounds that scored well with STAT1 were eliminated and the remaining ones were clustered using MOE (Molecular Operating Environment) program and visually examined using the UCSF Chimera ViewDock function. Final 100 compounds were selected based on the combination of GRID and AMBER score, drug likeness (Lipinski's rule of five), and on consideration of maximizing compounds from different clusters.

Molecular Dynamics Simulation and Calculation of Binding Free Energy.

The binding free energies of inS3-54 to STAT3 and STAT1 were performed by 3-ns MD simulations followed by energy analysis using GBSA method as we previously described. Briefly, a total of 20 snapshots were collected from the production trajectory for molecular mechanic (MM)-GBSA free energy calculations using the formula $\Delta Gbind=Gcomplex-GSTAT-GinS3-54$, where $G=Gsolute+Gsolvent$.

STAT3-Dependent Luciferase Assay.

In this and all following assays, candidate compounds were dissolved and completely soluble in DMSO at 20 mM as a stock solution. MDA-MB-231-STAT3 stable cell line with high level of STAT3-dependent luciferase expression was exposed to candidate compounds at 20 µM in DMSO for 48 hours based on previous studies, and luciferase activity was measured using a luciferase assay kit (Promega, USA), following manufacturer's instructions. The final DMSO concentration in this and following assays was 0.1% (vol/vol).

Cytotoxicity and Apoptosis Assay.

Cytotoxicity of inS3-54 was determined using sulphorhodamine colorimetric assay as described previously (41). Photometric enzyme immunoassay using Cell Death Detection ELISA Plus kit (Roche Diagnostics, Indianapolis, Ind.) was performed for quantitative in-vitro determination of cytoplasmic histone-associated DNA fragments and apoptosis as we previously described.

Electrophoretic Mobility Shift Assay (EMSA).

H1299 cells were transiently transfected with FLAG-tagged STAT3 or STAT1 expression construct. Forty-eight hours following transfection, cells were harvested and lysed with 3 cycles of freeze and thaw. 10-20 µg lysate was mixed with 2 µg poly (dI-dC), 1 µg BSA in binding buffer (10 mM HEPES, pH7.9, 50 mM KCl, 10% Glycerol, 0.2 mg/ml BSA, 1 mM DTT and 0.2 mM PMSF), and $4 \times 10^4$ cpm [32P]-labeled SIE probe in a total volume of 20 µL. The mixture was incubated for 20 minutes at room temperature and separated on 6% non-denaturing PAGE. The signal was detected by autoradiography. For supershift and competition, 2 µL specific antibodies against STAT3 or STAT1 or 100-fold cold SIE probe (5'-AGCTTCATTTCCCGTAAATCCCTA-3'-SEQ ID NO: 1) was added to the reaction mixture and incubated for 30 minutes before adding labeled SIE probe. To determine the effect of inS3-54 on STAT3 or STAT1 binding to SIE probe, inS3-54 was first diluted with DMSO and equal volume of diluted inS3-54 was added to the reaction mixture followed by incubation at room temperature for 30 minutes before incubating with the labeled SIE probe.

Conjugation of inS3-54 and Pull-Down Assay.

EAH-Sepharose 4B containing free amino groups with 11-atom spacer arms was used to couple inS3-54 with the carbodiimide coupling method according to manufacturer's instructions. Control EAH Sepharose was prepared exactly the same way without inS3-54. Since inS4-54 is orange in color, the conjugation of inS3-54 to EAH Sepharose 4B was verified by monitoring the color change of EAH beads.

For pull-down assay, inS3-54-conjugated and control beads equilibrated with binding buffer (10 mM MES/NaOH, pH 6.5, 150 mM NaCl, 2 mM MgCl2, 2 mM CaCl2, 5 mM KCl, 0.5% NP-40) were blocked with 10% milk in the binding buffer containing 0.2 mM PMSF and protease inhibitor cocktails followed by incubation with 60 µg lysate of H1299 cells harboring FLAG-STAT3 at room temperature for 1 hour. The unbound proteins were removed by washing for 7 times and the bound proteins were separated by SDS-PAGE followed by analysis using Western blot or silver staining. For competition analysis, cell lysate was pre-incubated with 10 µM inS3-54, DMSO vehicle, or an irrelevant compound control at room temperature for 1 hour prior to the pull-down assay.

Migration and Invasion Assay.

For wound-healing assay, $1 \times 10^5$ cells per well were plated in 6-well plates followed by introduction of a wound and monitoring the healing process of the wound over a 24-hour period. The healing of the wound was determined by measuring the remaining gap between two migrating edges at different times. Cell invasion assay was performed using Matrigel-coated Boyden Chambers (BD Biosciences, Bedford, Mass.) according to manufacturer's instructions. At different times, invading cells were stained with crystal violate and counted.

Subcellular Fractionation.

Subcellular fractionation was performed as previously described. Briefly, cells were lysed in 10 mM HEPES, pH7.9, 10 mM KCl, 1.5 mM MgCl2, 0.34 M Sucrose, 10% glycerol, 1% Triton X-100, 1 mM DTT, 10 µM leupeptin, protease inhibitor cocktail and centrifuged at 4,200 g for 5 minutes to collect supernatant as cytosolic fraction. The pellet (nuclei) was resuspended in 3 mM EDTA, 0.2 mM EGTA, 1 mM DTT, 10 µM leupeptin, protease inhibitor cocktail and incubated on ice for 30 minutes followed by centrifugation at 5,000 g for 5 minutes. The supernatant was collected as soluble nuclear fraction. The pellet was resuspended in 50 mM Tris/HCl, pH7.4, 150 mM NaCl, 0.5% NP-50, 5 mM EDTA, 50 mM NaF, 1 mM NaVO3, 1% SDS, 1 mM DTT, 10 µM leupeptin, protease inhibitor cocktail and sonicated to release proteins from chromatins.

Quantitative RT-PCR.

Quantitative RT-PCR analysis was performed using primers shown in supplemental Table 2 as previously described.

TABLE 2

| | Primers for real-time PCR | | |
|---|---|---|---|
| STAT3 | F: | GGCCCCTCGTCATCAAGA | SEQ ID NO: 3 |
| | R: | TTTGACCAGCAACCTGACTTTAGT | SEQ ID NO: 4 |
| CyclinD1 | F: | CTTCCTCTCCAAAATGCCAG | SEQ ID NO: 5 |
| | R: | AGAGATGGAAGGGGGAAAGA | SEQ ID NO: 6 |
| Survivin | F: | TGCCTGGCAGCCCTTTC | SEQ ID NO: 7 |
| | R: | CCTCCAAGAAGGGCCAGTTC | SEQ ID NO: 8 |
| VEGF | F: | TACCTCCACCATGCCAAGTG | SEQ ID NO: 9 |
| | R: | GATGATTCTGCCCTCCTCCTT | SEQ ID NO: 10 |
| MMP-1 | F: | AGCTAGCTCAGGATGACATTGATG | SEQ ID NO: 11 |
| | R: | GCCGATGGGCTGGACAG | SEQ ID NO: 12 |

TABLE 2-continued

Primers for real-time PCR

| | | | |
|---|---|---|---|
| MMP-2 | F: | TAGCATGTCCCTACCGAGTCT | SEQ ID NO: 13 |
| | R: | ATTGGATGGCAGTAGCTGC | SEQ ID NO: 14 |
| MMP-9 | F: | TGACAGCGACAAGAAGTG | SEQ ID NO: 15 |
| | R: | CAGTGAAGCGGTACATAGG | SEQ ID NO: 16 |
| MMP-10 | F: | ATCCAAGAGGCATCCATACC | SEQ ID NO: 17 |
| | R: | TCAACCTTAGGCTCAACTCC | SEQ ID NO: 18 |
| Twist | F: | CGGGAGTCCGCAGTCTTA | SEQ ID NO: 19 |
| | R: | TGAATCTTGCTCAGCTTGTC | SEQ ID NO: 20 |
| GAPDH | F: | AAGGACTCATGACCACAGTCCAT | SEQ ID NO: 21 |
| | R: | CCATCACGCCACAGTTTCC | SEQ ID NO: 22 |

The threshold cycles (Ct) were determined and normalized against that of GAPDH internal control. The relative mRNA levels were shown as the value of $2\Delta Ct$.

Example 2

Identification and Characterization of inS3-54 Analogues

To investigate the SAR of the small molecule inhibitor, inS3-54, targeting the DBD of human STAT3 and to help identify a lead compound for further development, we searched the virtual Chemdiv database for inS3-54 analogues with a criterion of 80% structural similarity using the Chemfinder module in Chemoffice 8.0. Total 79 commercially available analogues were identified (Table 3).

TABLE 3

Chemical properties of inS3-54 and its analogues

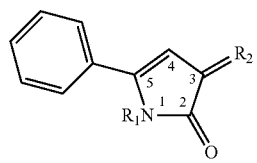

Core Structure

| Compound | $R_1$ | $R_2$ | Formula | M.W. (g/mol) |
|---|---|---|---|---|
| inS3-54 | 4-carboxyphenyl-methyl | 4-nitrophenyl-methyl | $C_{24}H_{16}N_2O_5$ | 412.41 |
| A1 | —H | N-methyl-anilino | $C_{18}H_{16}N_2O$ | 276.33 |
| A2 | 3-carboxyphenyl-methyl | 5-(2,5-dichlorophenyl)furan-2-yl-methyl | $C_{28}H_{17}Cl_2NO_4$ | 502.34 |
| A3 | 2-methyl-5-nitrophenyl-methyl | 5-(2,5-dichlorophenyl)furan-2-yl-methyl | $C_{28}H_{18}ClN_2O_4$ | 517.36 |
| A4 | 4-methylphenyl | 5-(4-nitrophenyl)furan-2-yl-methyl | $C_{28}H_{20}N_2O_4$ | 448.47 |
| A5 | 2,4-dimethylphenyl | 5-(4-nitrophenyl)furan-2-yl-methyl | $C_{29}H_{22}N_2O_4$ | 462.50 |

TABLE 3-continued

Chemical properties of inS3-54 and its analogues

Core Structure

| Compound | R₁ | R₂ | Formula | M.W. (g/mol) |
|---|---|---|---|---|
| A6 | 4-Cl-phenyl | 5-(4-nitrophenyl)furan-2-yl carbonyl | $C_{27}H_{17}ClN_2O_4$ | 468.89 |
| A7 | 4-methoxyphenyl | 5-(4-nitrophenyl)furan-2-yl carbonyl | $C_{28}H_{20}N_2O_5$ | 464.47 |
| A8 | 3-acetylphenyl | 5-(4-nitrophenyl)furan-2-yl carbonyl | $C_{29}H_{20}N_2O_5$ | 476.48 |
| A9 | 2,3-dimethylphenyl | 5-(4-nitrophenyl)furan-2-yl carbonyl | $C_{28}H_{20}N_2O_4$ | 448.47 |
| A10 | 3-Cl-phenyl | 5-(4-nitrophenyl)furan-2-yl carbonyl | $C_{27}H_{17}ClN_2O_4$ | 468.88 |
| A11 | 4-F-phenyl | 5-(4-nitrophenyl)furan-2-yl carbonyl | $C_{27}H_{17}FN_2O_4$ | 452.43 |
| A12 | 3-methoxyphenyl | 5-(4-nitrophenyl)furan-2-yl carbonyl | $C_{28}H_{20}N_2O_5$ | 464.47 |
| A13 | 3-nitrophenyl | 5-(4-nitrophenyl)furan-2-yl carbonyl | $C_{27}H_{17}N_3O_6$ | 479.44 |

TABLE 3-continued

Chemical properties of inS3-54 and its analogues

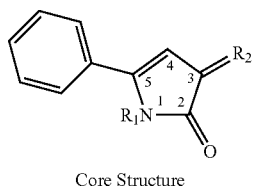

Core Structure

| Compound | R₁ | R₂ | Formula | M.W. (g/mol) |
|---|---|---|---|---|
| A14 | 2-chlorophenyl | 5-methyl-2-(4-nitrophenyl)furan | $C_{27}H_{17}ClN_2O_4$ | 468.89 |
| A15 | phenyl | 4-chlorophenyl | $C_{23}H_{16}ClNO$ | 357.83 |
| A16 | 4-chlorophenyl | 4-chlorophenyl | $C_{23}H_{15}Cl_2NO$ | 392.28 |
| A17 | 4-methoxyphenyl | 4-chlorophenyl | $C_{24}H_{18}ClNO_2$ | 387.86 |
| A18 | 4-hydroxyphenyl | 4-chlorophenyl | $C_{23}H_{16}ClNO_2$ | 373.83 |
| A19 | 3-(methoxycarbonyl)phenyl | 4-chlorophenyl | $C_{25}H_{18}ClNO_3$ | 415.87 |
| A20 | 4-biphenyl | 4-chlorophenyl | $C_{29}H_{20}ClNO$ | 433.93 |
| A21 | 4-tert-butylphenyl | 4-chlorophenyl | $C_{27}H_{24}ClNO$ | 413.94 |
| A22 | 4-fluorophenyl | 4-chlorophenyl | $C_{23}H_{15}ClFNO$ | 375.82 |
| A23 | 4-(methoxycarbonyl)phenyl | 4-chlorophenyl | $C_{25}H_{18}ClNO_3$ | 415.87 |
| A24 | 3-nitrophenyl | 4-chlorophenyl | $C_{23}H_{15}ClN_2O_3$ | 402.83 |

TABLE 3-continued

Chemical properties of inS3-54 and its analogues

Core Structure

| Compound | R$_1$ | R$_2$ | Formula | M.W. (g/mol) |
|---|---|---|---|---|
| A25 | 2,5-dimethyl-nitrophenyl | 4-chlorophenyl | C$_{24}$H$_{17}$ClN$_2$O$_3$ | 416.86 |
| A26 | 4-(acetamido)phenyl | 4-chlorophenyl | C$_{25}$H$_{19}$ClN$_2$O$_2$ | 414.88 |
| A27 | 2-chlorophenyl | 4-chlorophenyl | C$_{23}$H$_{15}$Cl$_2$NO | 392.28 |
| A28 | 4-(phenylamino)phenyl | 4-chlorophenyl | C$_{29}$H$_{21}$ClN$_2$O | 448.94 |
| A29 | 3,4-dimethylphenyl | 4-nitrophenyl | C$_{25}$H$_{20}$N$_2$O$_3$ | 396.44 |
| A30 | 3,4-dimethylphenyl | 4-nitrophenyl | C$_{25}$H$_{20}$N$_2$O$_3$ | 396.44 |
| A31 | 4-chlorophenyl | 4-nitrophenyl | C$_{23}$H$_{15}$ClN$_2$O$_3$ | 402.83 |
| A32 | 2-methoxyphenyl | 4-nitrophenyl | C$_{24}$H$_{18}$N$_2$O$_4$ | 398.41 |
| A33 | 4-methoxyphenyl | 4-nitrophenyl | C$_{24}$H$_{18}$N$_2$O$_4$ | 398.41 |

TABLE 3-continued

Chemical properties of inS3-54 and its analogues

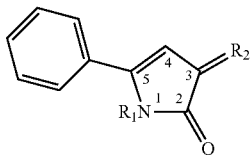

Core Structure

| Compound | R₁ | R₂ | Formula | M.W. (g/mol) |
|---|---|---|---|---|
| A34 | 3-(methoxycarbonyl)phenyl | 4-nitrophenyl | $C_{25}H_{18}N_2O_5$ | 426.42 |
| A35 | 4-biphenyl | 4-nitrophenyl | $C_{29}H_{20}N_2O_3$ | 444.48 |
| A36 | benzyl | 4-nitrophenyl | $C_{24}H_{18}N_2O_3$ | 382.41 |
| A37 | 3,4-dimethylphenyl | 4-nitrophenyl | $C_{25}H_{20}N_2O_3$ | 396.44 |
| A38 | 3-chlorophenyl | 4-nitrophenyl | $C_{23}H_{15}ClN_2O_3$ | 402.83 |
| A39 | 3,4-dichlorophenyl | 4-nitrophenyl | $C_{23}H_{14}Cl_2N_2O_3$ | 437.27 |
| A40 | 4-fluorophenyl | 4-nitrophenyl | $C_{23}H_{15}FN_2O_3$ | 386.38 |
| A41 | 3-methoxyphenyl | 4-nitrophenyl | $C_{24}H_{18}N_2O_4$ | 398.41 |
| A42 | 3-hydroxyphenyl | 4-nitrophenyl | $C_{23}H_{16}N_2O_4$ | 384.38 |

TABLE 3-continued

Chemical properties of inS3-54 and its analogues

Core Structure

| Compound | R₁ | R₂ | Formula | M.W. (g/mol) |
|---|---|---|---|---|
| A43 | 4-methylphenyl methyl benzoate | 4-methyl-nitrobenzene | $C_{25}H_{18}N_2O_5$ | 426.42 |
| A44 | 3-methyl-nitrobenzene | 4-methyl-nitrobenzene | $C_{23}H_{15}N_3O_5$ | 413.38 |
| A45 | 4-methyl-N,N-diethylaniline | 4-methyl-nitrobenzene | $C_{27}H_{25}N_3O_3$ | 439.51 |
| A46 | 6-methylnaphthalene | 4-methyl-nitrobenzene | $C_{27}H_{18}N_2O_3$ | 418.44 |
| A47 | 4-methyl-acetanilide | 4-methyl-nitrobenzene | $C_{25}H_{19}N_3O_4$ | 425.44 |
| A48 | 3,4-dichloro-methylbenzene | 4-methyl-nitrobenzene | $C_{23}H_{14}Cl_2N_2O_3$ | 437.27 |
| A49 | 4-methyl-N-phenylaniline | 4-methyl-nitrobenzene | $C_{29}H_{21}N_3O_3$ | 459.50 |
| A50 | 3-methyl methyl benzoate | 4-methylanisole | $C_{26}H_{21}NO_4$ | 411.45 |
| A51 | 1-methylnaphthalene | 4-methylanisole | $C_{28}H_{21}NO_2$ | 403.47 |

TABLE 3-continued

Chemical properties of inS3-54 and its analogues

Core Structure

| Compound | R₁ | R₂ | Formula | M.W. (g/mol) |
|---|---|---|---|---|
| A52 | 3,4-dichlorobenzyl | 4-methoxybenzyl | $C_{24}H_{17}Cl_2NO_2$ | 422.30 |
| A53 | 4-fluorobenzyl | 4-methoxybenzyl | $C_{24}H_{18}FNO_2$ | 371.40 |
| A54 | 4-(methoxycarbonyl)benzyl | 4-methoxybenzyl | $C_{26}H_{21}NO_4$ | 411.45 |
| A55 | 4-((4-nitrophenyl)thio)benzyl | (5-methylfuran-2-yl)-2,5-dichlorophenyl | $C_{30}H_{33}N_2O_4S$ | 506.57 |
| A56 | naphthalen-2-ylmethyl | 4-methoxybenzyl | $C_{28}H_{21}NO_2$ | 403.47 |
| A57 | 2-chlorobenzyl | 4-methoxybenzyl | $C_{24}H_{18}ClNO_2$ | 387.86 |
| A58 | 2,3-dichlorobenzyl | 4-methoxybenzyl | $C_{24}H_{17}ClN_2O_2$ | 422.30 |
| A59 | naphthalen-2-ylmethyl | 4-chlorobenzyl | $C_{27}H_{18}ClNO$ | 407.89 |
| A60 | 4-acetamidobenzyl | 4-methoxybenzyl | $C_{26}H_{22}N_2O_3$ | 410.46 |

TABLE 3-continued

Chemical properties of inS3-54 and its analogues

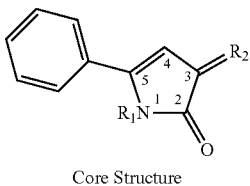

Core Structure

| Compound | R₁ | R₂ | Formula | M.W. (g/mol) |
|---|---|---|---|---|
| A61 | 4-methylbenzoic acid | 5-methyl-2-(3,4-dichlorophenyl)furan | $C_{28}H_{17}Cl_2NO_4$ | 502.34 |
| A62 | 4-methylphenyl | 5-methyl-2-(4-nitrophenyl)furan | $C_{27}H_{18}N_2O_4$ | 434.44 |
| A63 | 2-hydroxy-5-methylphenyl acetyl | 5-methyl-2-(4-nitrophenyl)furan | $C_{28}H_{18}N_2O_7$ | 494.45 |
| A64 | 4-ethylphenyl | 5-methyl-2-(4-nitrophenyl)furan | $C_{28}H_{20}N_2O_4$ | 448.47 |
| A65 | 3-acetylphenyl | 4-chlorophenyl | $C_{25}H_{18}ClNO_2$ | 399.87 |
| A66 | methyl 2-chloro-5-methylbenzoate | 4-chlorophenyl | $C_{25}H_{17}Cl_2NO_3$ | 450.31 |
| A67 | 4-(diethylamino)phenyl | 4-chlorophenyl | $C_{27}H_{15}ClN_2O$ | 428.95 |
| A68 | 4-methylphenyl | 4-nitrophenyl | $C_{23}H_{16}N_2O_3$ | 368.38 |
| A69 | 4-hydroxyphenyl | 4-nitrophenyl | $C_{23}H_{16}N_2O_4$ | 384.38 |

TABLE 3-continued

Chemical properties of inS3-54 and its analogues

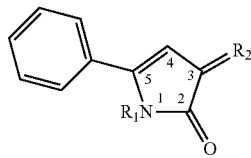

Core Structure

| Compound | R₁ | R₂ | Formula | M.W. (g/mol) |
|---|---|---|---|---|
| A70 | 5-methyl-2-hydroxy-benzoic acid (3-methyl-4-hydroxy-benzoic acid derivative) | 4-nitrophenyl | $C_{24}H_{16}N_2O_6$ | 428.39 |
| A71 | 3-acetylphenyl | 4-methoxyphenyl | $C_{25}H_{18}N_2O_4$ | 410.42 |
| A72 | 4-hydroxyphenyl | 4-methoxyphenyl | $C_{24}H_{19}NO_3$ | 369.41 |
| A73 | 2-hydroxyphenyl | 4-methoxyphenyl | $C_{24}H_{19}NO_3$ | 369.41 |
| A74 | 4-(ethoxycarbonyl)phenyl | 4-chlorophenyl | $C_{26}H_{20}ClNO_3$ | 429.89 |
| A75 | 2-methoxyphenyl | 4-chlorophenyl | $C_{24}H_{18}ClNO_2$ | 387.86 |
| A76 | 3-chlorophenyl | 4-chlorophenyl | $C_{23}H_{15}Cl_2NO$ | 392.28 |
| A77 | 4-(dimethylamino)phenyl | 4-nitrophenyl | $C_{25}H_{21}N_3O_3$ | 411.45 |
| A78 | 4-(dimethylamino)phenyl | 4-methoxyphenyl | $C_{26}H_{24}N_2O_2$ | 396.48 |

TABLE 3-continued

Chemical properties of inS3-54 and its analogues

Core Structure

| Compound | R₁ | R₂ | Formula | M.W. (g/mol) |
|---|---|---|---|---|
| A79 | | (full structure shown) | $C_{23}H_{22}N_2O_6$ | 422.43 |
| A80 | 4-bromophenyl | 4-chlorophenyl | $C_{19}H_{15}ClBrNO_4$ | 436.68 |
| A81 | 4-biphenyl | 4-chlorophenyl | $C_{25}H_{20}ClNO_4$ | 433.88 |
| A82 | 4-methyl-2-hydroxy-benzoic acid | 4-chlorophenyl | $C_{20}H_{16}ClNO_7$ | 417.80 |
| A83 | 2-hydroxy-3-carboxy-5-methylphenyl | 4-chlorophenyl | $C_{20}H_{16}ClNO_7$ | 417.80 |
| A84 | benzyl | 4-chlorophenyl | $C_{20}H_{18}ClNO_4$ | 371.81 |
| A85 | 4-sulfophenyl | 4-chlorophenyl | $C_{19}CH_{16}ClNO_7S$ | 437.85 |
| A86 | 4-ethoxyphenyl | 2-chlorophenyl | $C_{21}H_{20}ClNO_5$ | 401.84 |
| A87 | 4-ethoxyphenyl | 4-biphenyl | $C_{27}H_{25}NO_5$ | 443.49 |

TABLE 3-continued

Chemical properties of inS3-54 and its analogues

Core Structure

| Compound | R₁ | R₂ | Formula | M.W. (g/mol) |
|---|---|---|---|---|
| A88 | 4-methylphenyl-CH₂-C(O)-OH substituent | 4-chlorophenyl | $C_{26}H_{20}ClBrN_2O_6$ | 571.80 |
| A89 | (structure with 4-chlorophenyl, ethyl ester, 4-nitrobenzyloxy, N-4-bromophenyl) | | $C_{21}H_{18}ClNO_6$ | 415.82 |

Figure 12:
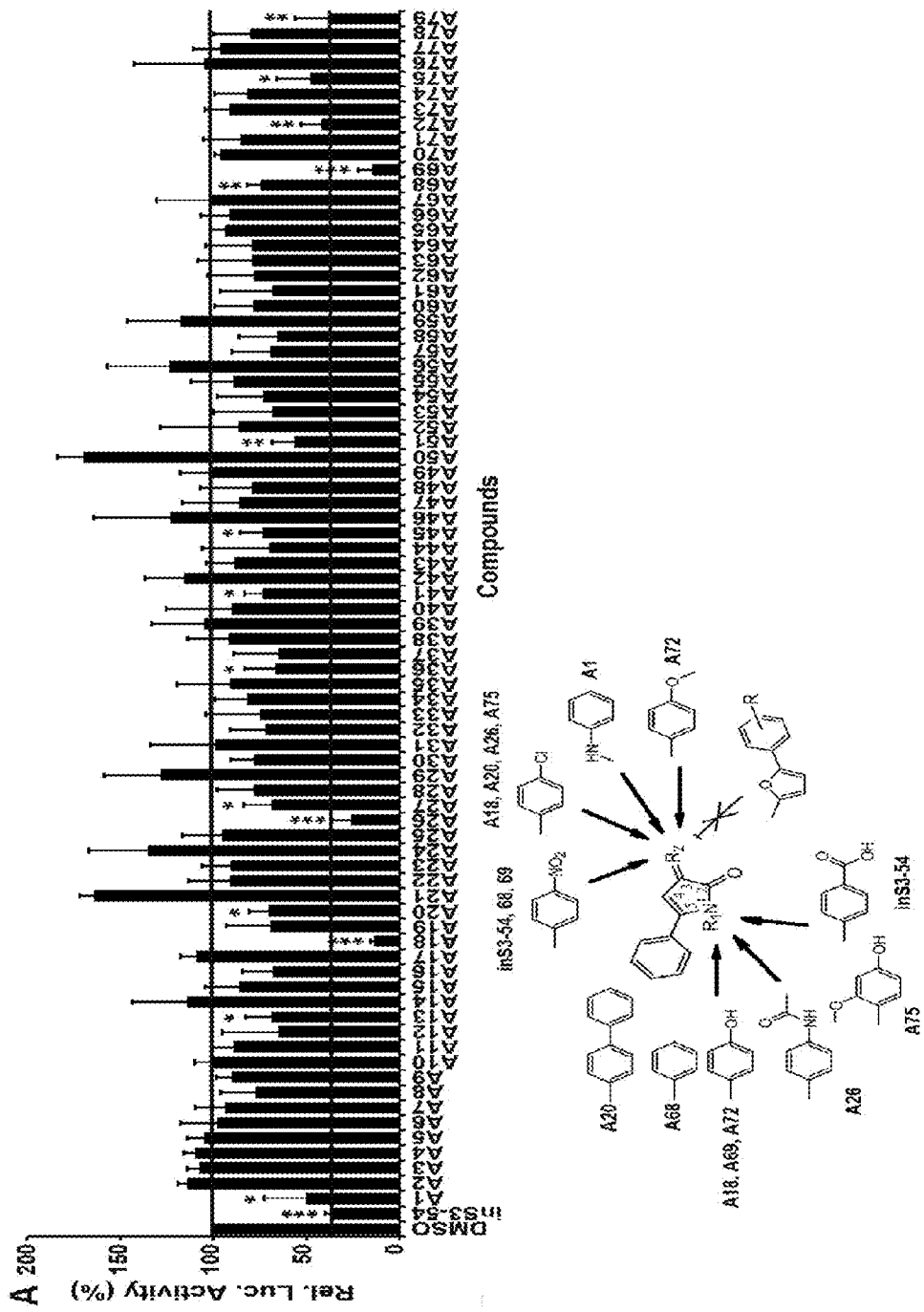
FIG. 12. Identification of active inS3-54 analogues. (A) Effects of inS3-54 analogues on STAT3-dependent luciferase expression. MDA-MB-231 cells with stable STAT3-dependent luciferase expression were treated with DMSO control, 20 µM inSTAT3-54 or its analogues (A1-A79), followed by measurement of luciferase activity. (*p<0.05; p<0.01; *p<0.001).

These analogues were acquired and tested first for their activity in suppressing STAT3-dependent luciferase expression in comparison with inS3-54 and DMSO vehicle controls. FIG. 12A and Table 4 show that 15 analogues (A1, 13, 18, 20, 26, 27, 36, 41, 45, 51, 68, 69, 72, 75, and 79) significantly inhibited luciferase expression compared to DMSO vehicle control. By "significant" we mean the analogues inhibited luciferase expression statistically significant with p value less than 0.05. Among these 15 analogues, 3 (A18, 26, and 69) are more potent than the original compound inS3-54. Consequently, A18, A26 and A69 were selected for further testing. Structural analysis of all 79 analogues revealed potential activating and inhibitory side groups (FIG. 12B).

TABLE 4

Relative Luciferase Activity
Rel. luciferase activity (%)

| Treatment | 1 | 2 | 3 | 4 | Mean | SD | P value |
|---|---|---|---|---|---|---|---|
| DMSO | 100.0 | 100.0 | 100.0 | | 100.0 | 0.0 | 0 |
| inS3-54 | 34.2 | 37.2 | 41.0 | | 37.5 | 3.4 | 0.000 |
| A1 | 47.3 | 23.8 | 79.6 | | 50.2 | 28.0 | 0.037 |
| A2 | 120.3 | 107.5 | 114.1 | | 114.0 | 6.4 | 0.019 |
| A3 | 116.7 | 104.0 | 101.3 | | 107.3 | 8.2 | 0.198 |
| A4 | 117.8 | 108.4 | 103.4 | | 109.9 | 7.3 | 0.079 |
| A5 | 113.5 | 109.3 | 92.2 | | 105.0 | 11.3 | 0.484 |
| A6 | 110.9 | 112.7 | 71.0 | | 98.2 | 23.6 | 0.901 |
| A7 | 99.6 | 109.4 | 72.3 | | 93.8 | 19.3 | 0.605 |
| A8 | 71.9 | 102.6 | 57.5 | | 77.3 | 23.0 | 0.163 |
| A9 | 78.4 | 95.8 | 96.2 | | 90.2 | 10.2 | 0.169 |
| A10 | 87.4 | 110.4 | 103.7 | | 100.5 | 11.8 | 0.945 |
| A11 | 73.5 | 101.5 | 91.7 | | 88.9 | 14.2 | 0.248 |
| A12 | 34.2 | 105.8 | 55.4 | | 65.1 | 36.8 | 0.176 |
| A13 | 67.6 | 86.4 | 52.2 | | 68.7 | 17.1 | 0.034 |
| A14 | 140.4 | 129.3 | 72.3 | | 114.0 | 36.5 | 0.544 |
| A15 | 98.4 | 99.9 | 60.1 | | 86.1 | 22.6 | 0.348 |
| A16 | 55.8 | 91.2 | 57.1 | | 68.0 | 20.1 | 0.051 |
| A17 | 103.2 | 120.5 | 104.2 | | 109.3 | 9.7 | 0.172 |
| A18 | 16.3 | 13.2 | 12.3 | | 14.0 | 2.1 | 0.000 |
| A19 | 45.7 | 101.8 | 60.1 | | 69.2 | 29.2 | 0.141 |
| A20 | 63.2 | 85.1 | 63.8 | | 70.7 | 12.5 | 0.015 |
| A21 | 158.0 | 174.7 | 159.1 | | 163.9 | 9.3 | 0.000 |
| A22 | 97.9 | 114.0 | 61.1 | | 91.0 | 27.1 | 0.596 |
| A23 | 99.2 | 103.2 | 69.4 | | 90.6 | 18.4 | 0.427 |
| A24 | 152.4 | 162.1 | 90.8 | | 135.1 | 38.6 | 0.191 |
| A25 | 74.6 | 124.2 | 87.8 | | 95.6 | 25.7 | 0.780 |
| A26 | 38.0 | 27.5 | 13.2 | | 26.2 | 12.4 | 0.001 |
| A27 | 48.5 | 83.6 | 74.2 | | 68.8 | 18.2 | 0.041 |
| A28 | 67.2 | 106.0 | 62.1 | | 78.4 | 24.0 | 0.194 |
| A29 | 100.7 | 170.4 | 113.3 | | 128.1 | 37.2 | 0.260 |
| A30 | 89.6 | 83.9 | 61.2 | | 78.2 | 15.0 | 0.066 |
| A31 | 122.8 | 124.5 | 49.9 | | 99.1 | 42.6 | 0.971 |
| A32 | 58.2 | 99.2 | 58.6 | | 72.0 | 23.6 | 0.109 |
| A33 | 33.8 | 92.3 | 99.1 | | 75.1 | 35.9 | 0.296 |
| A34 | 61.1 | 103.6 | 80.8 | | 81.9 | 21.3 | 0.214 |
| A35 | 51.3 | 109.5 | 112.6 | | 91.1 | 34.5 | 0.680 |
| A36 | 46.4 | 87.4 | 66.3 | | 66.7 | 20.5 | 0.048 |
| A37 | 31.9 | 86.2 | 77.2 | | 65.1 | 29.1 | 0.107 |
| A38 | 66.5 | 119.9 | 88.8 | | 91.8 | 26.8 | 0.623 |
| A39 | 119.6 | 129.6 | 65.9 | | 105.1 | 34.3 | 0.810 |
| A40 | 126.5 | 101.5 | 43.0 | | 90.3 | 42.9 | 0.716 |
| A41 | 60.5 | 79.5 | 81.2 | | 73.7 | 11.5 | 0.017 |
| A42 | 100.8 | 145.3 | 100.8 | | 115.6 | 25.7 | 0.352 |
| A43 | 98.6 | 100.4 | 66.9 | | 88.6 | 18.8 | 0.354 |
| A44 | 28.2 | 115.7 | 65.8 | | 69.9 | 43.9 | 0.301 |
| A45 | 60.9 | 89.3 | 71.6 | | 73.9 | 14.3 | 0.034 |
| A46 | 156.2 | 147.8 | 64.9 | | 122.9 | 50.4 | 0.475 |
| A47 | 106.8 | 108.8 | 43.3 | | 86.3 | 37.3 | 0.560 |
| A48 | 87.5 | 108.6 | 42.5 | | 79.5 | 33.8 | 0.352 |
| A49 | 93.7 | 124.2 | 90.2 | | 102.7 | 18.7 | 0.815 |
| A50 | 168.6 | 187.0 | 153.6 | | 169.7 | 16.7 | 0.002 |
| A51 | 42.2 | 71.0 | 56.6 | | 56.6 | 14.4 | 0.006 |

TABLE 4-continued

Relative Luciferase Activity
Rel. luciferase activity (%)

| Treatment | 1 | 2 | 3 | 4 | Mean | SD | P value |
|---|---|---|---|---|---|---|---|
| A52 | 39.5 | 141.9 | 77.7 | | 86.4 | 51.7 | 0.672 |
| A53 | 45.4 | 113.0 | 47.4 | | 68.6 | 38.5 | 0.231 |
| A54 | 77.8 | 100.8 | 41.7 | | 73.5 | 29.8 | 0.197 |
| A55 | 104.3 | 106.2 | 57.4 | | 89.3 | 27.7 | 0.539 |
| A56 | 150.7 | 143.4 | 76.2 | | 123.4 | 41.1 | 0.380 |
| A57 | 59.5 | 97.9 | 51.5 | | 69.6 | 24.8 | 0.101 |
| A58 | 78.9 | 81.8 | 36.8 | | 65.8 | 25.2 | 0.079 |
| A59 | 124.7 | 148.5 | 80.5 | | 117.9 | 34.5 | 0.419 |
| A60 | 70.7 | 107.0 | 58.9 | | 78.9 | 25.1 | 0.218 |
| A61 | 57.8 | 107.0 | 40.8 | | 68.5 | 34.4 | 0.188 |
| A62 | 71.1 | 111.3 | 52.2 | | 78.2 | 30.2 | 0.279 |
| A63 | 93.2 | 105.6 | 38.3 | | 79.1 | 35.8 | 0.369 |
| A64 | 79.8 | 109.6 | 49.0 | | 79.5 | 30.3 | 0.306 |
| A65 | 86.6 | 103.9 | 91.2 | | 93.9 | 9.0 | 0.305 |
| A66 | 90.3 | 110.5 | 73.6 | | 91.5 | 18.5 | 0.469 |
| A67 | 72.9 | 140.9 | 92.5 | | 102.1 | 35.0 | 0.923 |
| A68 | 71.2 | 84.5 | 68.7 | | 74.8 | 8.5 | 0.007 |
| A69 | 5.4 | 15.2 | 23.8 | | 14.8 | 9.2 | 0.000 |
| A70 | 99.0 | 97.9 | 92.8 | | 96.5 | 3.3 | 0.145 |
| A71 | 84.0 | 110.8 | 61.9 | | 85.6 | 24.5 | 0.365 |
| A72 | 34.2 | 58.1 | 34.1 | | 42.1 | 13.8 | 0.002 |
| A73 | 72.9 | 97.8 | 103.4 | | 91.3 | 16.2 | 0.407 |
| A74 | 65.9 | 105.7 | 74.5 | | 82.0 | 20.9 | 0.211 |
| A75 | 28.7 | 71.4 | 45.4 | | 48.5 | 21.6 | 0.014 |
| A76 | 60.0 | 151.4 | 104.0 | | 105.1 | 45.7 | 0.855 |
| A77 | 109.7 | 103.0 | 77.0 | | 96.6 | 17.3 | 0.750 |
| A78 | 71.7 | 107.9 | 61.0 | | 80.2 | 24.6 | 0.235 |
| A79 | 10.2 | 44.8 | 55.6 | | 36.9 | 23.7 | 0.010 |

Validation of Active Analogues.

Figure 14:
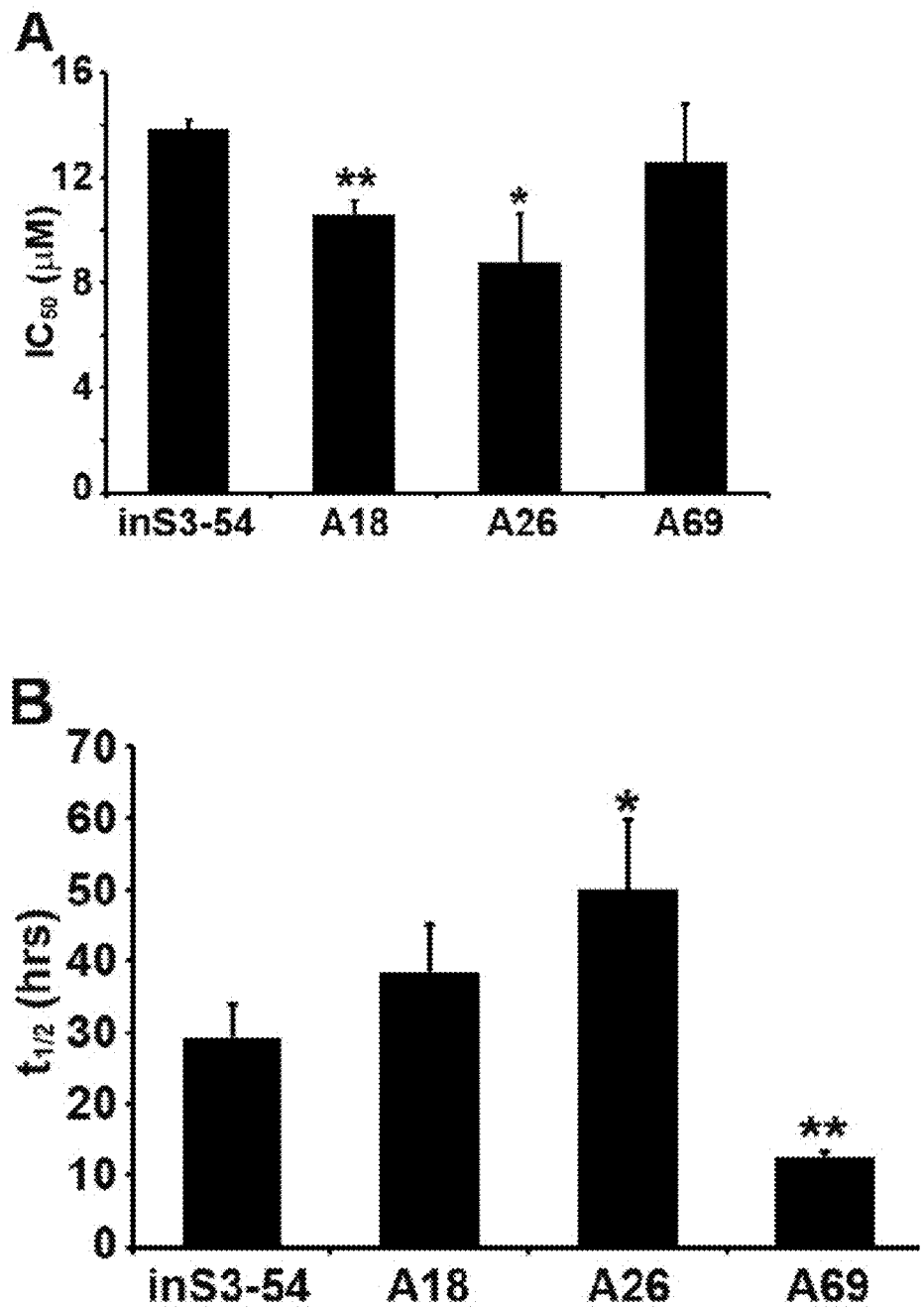
FIG. 14. Effects of inS3-54 analogues on STAT3-dependent and independent luciferase reporter expression. (A-B) $IC_{50}$ and $t_{1/2}$ of inS3-54 and its analogues in suppressing STAT3-dependent luciferase reporter expression in MDA-MB-231 cells. (C) Effect of inS3-54 and its analogues on expression luciferase reporter driven by a p27 promoter lacking STAT3-binding sequence.
Figure 14:
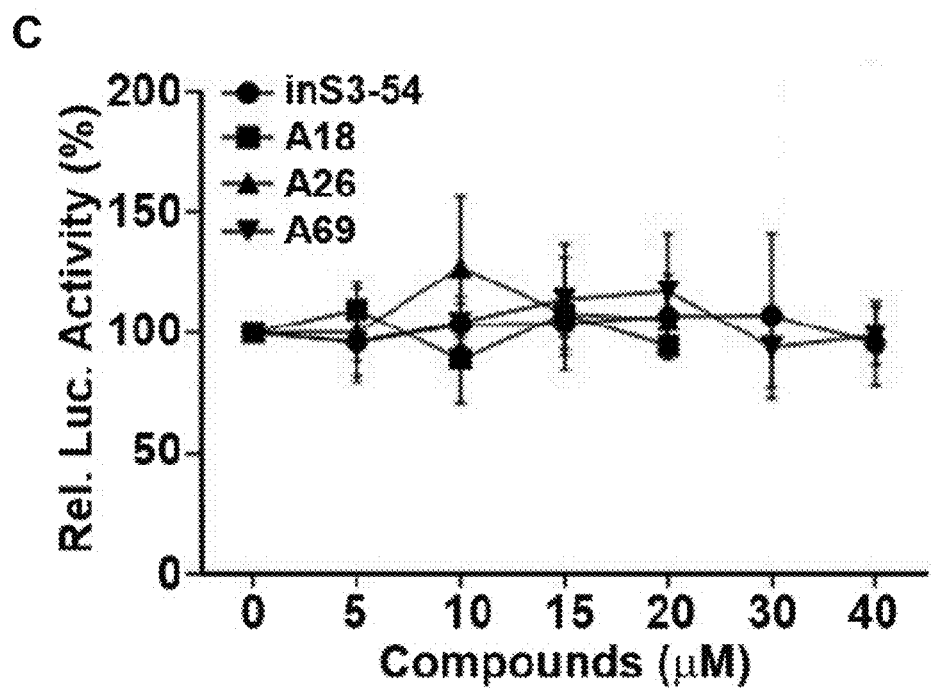

Next, we validated A18, A26, and A69 using newly synthesized compounds in the STAT3-dependent luciferase reporter assay. As shown in FIGS. 14A-B, newly synthesized A18, A26 and A69 all suppressed STAT3-dependent luciferase expression in dose-dependent and time-dependent manners with $IC_{50}$ values of 8.8-12.6 μM and $t_{1/2}$ of 12.7-49.9 hours. It appears that A18 and A26 has significant lower $IC_{50}$ than inS3-54. Although the $IC_{50}$ of A69 did not change from that of inS3-54, its $t_{1/2}$ is significantly lower. However, none of these three analogues inhibited the reporter expression driven by a p27 promoter containing no STAT3-binding site (FIG. 14C), suggesting that the inhibition of reporter expression by these compounds is unlikely due to non-specific effect on the reporter gene or due to cell death induced by the compounds.

Selectivity and Specificity of Active inS3-54 Analogues.

To investigate if the more potent analogues A18, A26, and A69 maintain selectivity for STAT3 over STAT1 as inS3-54, we performed electrophoretic mobility shift assay (EMSA) using [$^{32}$P]-labeled SIE probe and H1299 cells transiently transfected with FLAG-STAT3 or STAT1. As shown in FIG. 13A, the specific binding of DNA probe to STAT3 was demonstrated using super-shift and competition analyses. A18, A26, and A69 all inhibited the DNA-binding activity of STAT3 in a dose-dependent manner. The specific binding of DNA probe to STAT1 as shown by interference of binding using cold probe and STAT1 antibody that is known to interfere DNA-binding activity of STAT1, however, was not affected by smu of the analogues up to 100 μM. Thus, A18, A26, and A69 all selectively inhibit the DNA-binding activity of STAT3 over STAT1, similar as the parent compound inS3-54.

To further determine the specificity of these analogues, we performed colony formation assay of granulocyte macrophage, erythroid, and multi-potential hematopoietic progenitor cells isolated from bone marrow of $STAT3^{+/+}$ and $STAT3^{-/-}$ mice. Recently, it has been shown that STAT3 knock-out reduces 50-70% colony formation activity of granulocyte macrophage, erythroid, and multi-potential hematopoietic progenitor cells. We reasoned that a STAT3-specific inhibitor should not further reduce the proliferative activity $STAT3^{-/-}$ hematopoetic progenitor cells due to lack of STAT3 in these cells. As shown in FIG. 13B, all compounds reduced ~50-80% colony formation efficiency of hematopoietic progenitor cells from $STAT3^{+/+}$ mice. However, all three analogues had no significant effect on the colony formation of hematopoietic progenitor cells from $STAT3^{-/-}$ mice (FIG. 13C), suggesting that these analogues unlikely inhibit other targets important for proliferation of hematopoietic progenitor cells. Interestingly, inS3-54 further reduced the colony formation of these cells from $STAT3^{-/-}$ mice, indicating that inS3-54 may be less specific to STAT3 than its analogues.

InS3-54 Analogues Bind to STAT3.

Figure 15:
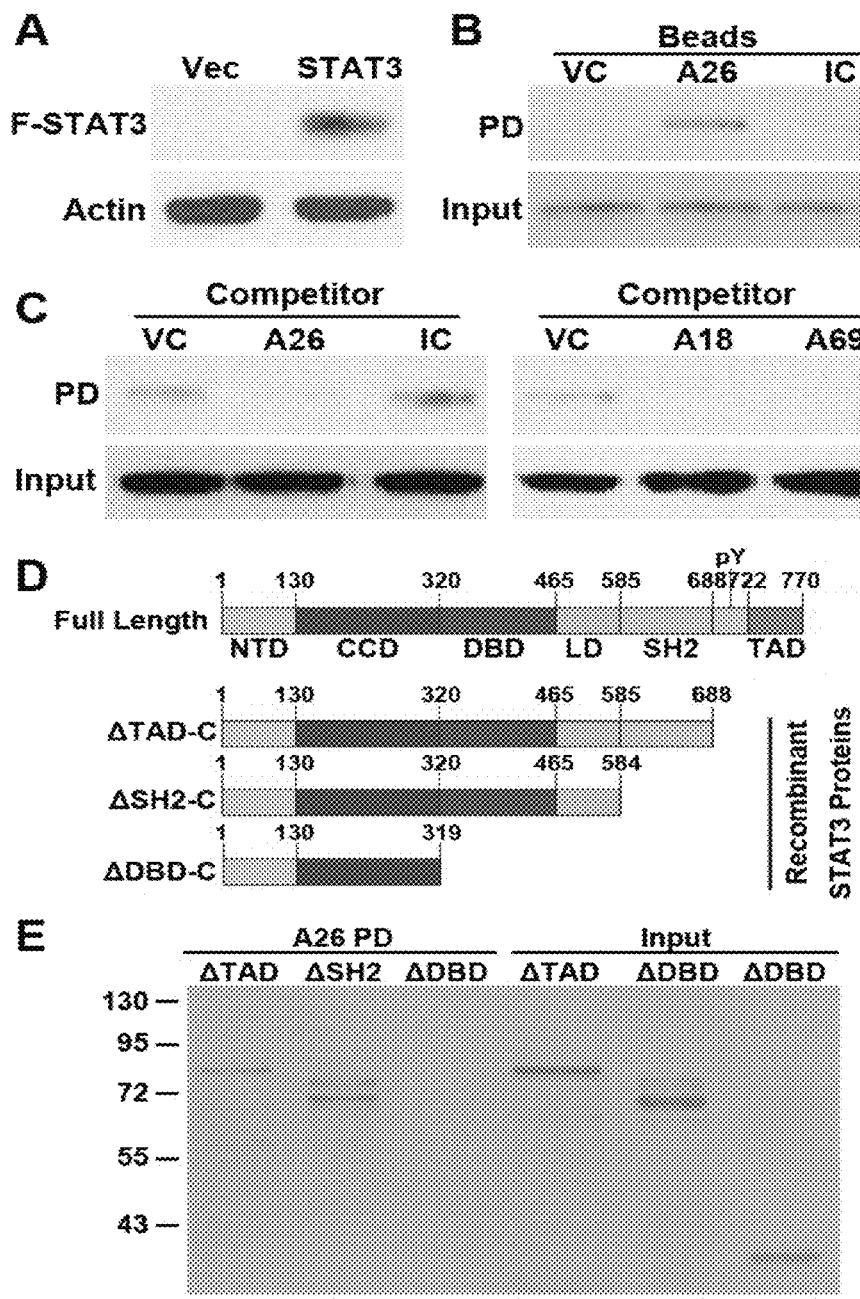
FIG. 15. Binding of inS3-54 analogues to STAT3. (A) Western blot analysis of STAT3 from total lysate of H1299 cells transfected with vector control (VC) or FLAG-STAT3 (STAT). (B) Pull-down assay of STAT3 from total lysate of FLAG-STAT3-transfected H1299 cells using Sepharose 4B-conjugated with vehicle control, A26 or an irrelevant compound (IC). Pull-down samples were separated using SDS-PAGE and Western blot analysis probed with anti-FLAG antibody. (C) Competition of STAT3-binding to A26-conjugated Sepharose 4B by excess vehicle control, or excess A18, A26, A69, or the irrelevant compound (IC). (D-E) Pull-down assay of recombinant STAT3. Purified STAT3 recombinant protein with different domains (D) were subjected to pull-down assay using A26-conjugated Sepharose 4B followed by separation on SDS-PAGE and revealed by silver staining (E). NTD=amino terminal domain; CCD=coiled coil domain; DBD=DNA-binding domain; LD=linker domain; SH2=SH2 domain; TAD=transactivation domain.

To determine if the active analogues (A18, A26 and A69) bind to STAT3, we took advantage of A26, which contains an imino group, and conjugated it to CNBr-activated Sepharose 4B. Successful conjugation of A26 to CNBr-activated Sepharose was confirmed by the change in color of the beads due to the intrinsic yellow color of A26. The A26-conjugated beads were then used to pull down STAT3 from lysate of Flag-STAT3-transfected H1299 cells followed by Western blot analysis as described previously. FIG. 15A shows the expression of Flag-STAT3. FIG. 15B shows that the A26-conjugated beads successfully pull down STAT3 whereas the vehicle control beads or the beads conjugated with an irrelevant compound do not. Furthermore, pretreatment of the cell lysate using excess free A26 inhibited the pull down of STAT3 by A26-conjugated beads but not by the irrelevant compound (FIG. 15C). To determine if A18 and A69 also bind to STAT3, we performed a similar competition analysis due to lack of usable group for immobilization of these compounds. As shown in FIG. 15C, both A18 and A69 completely inhibited STAT3 binding to A26-conjugated beads. Thus, we conclude that A18, A26, and A69 all bind to STAT3.

InS3-54 Analogue A26 Bind to the DBD of STAT3.

Although the parent compound inS3-54 was designed to bind to the DBD of STAT3, it is not known if its analogues bind directly to the DBD of STAT3. To eliminate the possibility that inS3-54 analogues bind to different domains of STAT3, we performed pull-down assays using purified recombinant STAT3 proteins with different domains (FIG. 15D) as targets. As shown in FIG. 15E, purified STAT3 proteins lacking carboxyl terminal domains including transactivation domain (ΔTAD) and SH2 domain (ΔSH2) were successfully pulled down by A26-conjugated beads. However, further deletion from carboxyl terminus including the DNA-binding domain (DBD) eliminated the pulldown by A26-conjugated beads. This finding suggests that A26 can directly bind to STAT3 and its binding site in STAT3 is likely located in DBD.

InS3-54 Analogues Inhibit Cancer Cell Survival by Inducing Apoptosis.

Figure 16:
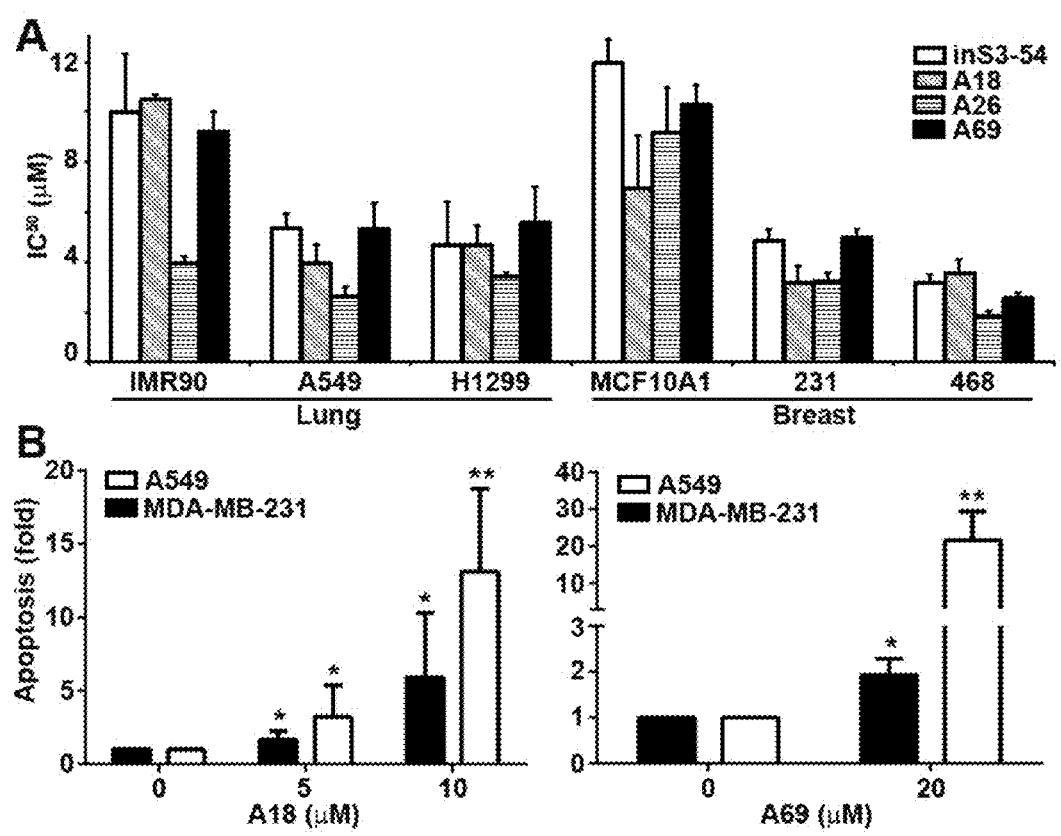
FIG. 16. Effect of active analogues on cancer cell proliferation and survival. (A) IC50 of inS3-54 and the active analogues (A18, A26, and A69) in different cell lines derived from dose-response curves using PrismPad program. (B) Apoptosis assay of exponentially growing A549 and MDA-MB-231 cells. (*p<0.05; **p<0.01).

To determine the effectiveness of the active analogues (A18, A26 and A69) in suppressing cancer cell survival and to determine the potential therapeutic window, we performed SRB assay of these compounds using cancer cells of lung (A549 and H1299) and breast (MDA-MB-231 and MDA-MB-468) as well as a non-cancerous mammary epithelial cell line (MCF10A1) and lung fibroblast cells (IMR90) in comparison with the parent compound inS3-54. FIG. 16A shows that the $IC_{50}$ of these compounds ranges 1.8-5.6 μM for cancer cells and 4.0-12.0 μM for noncancerous cells. The in-vitro therapeutic window for inS3-54, A18, and A69 ranges ~2-5

Figure 17:
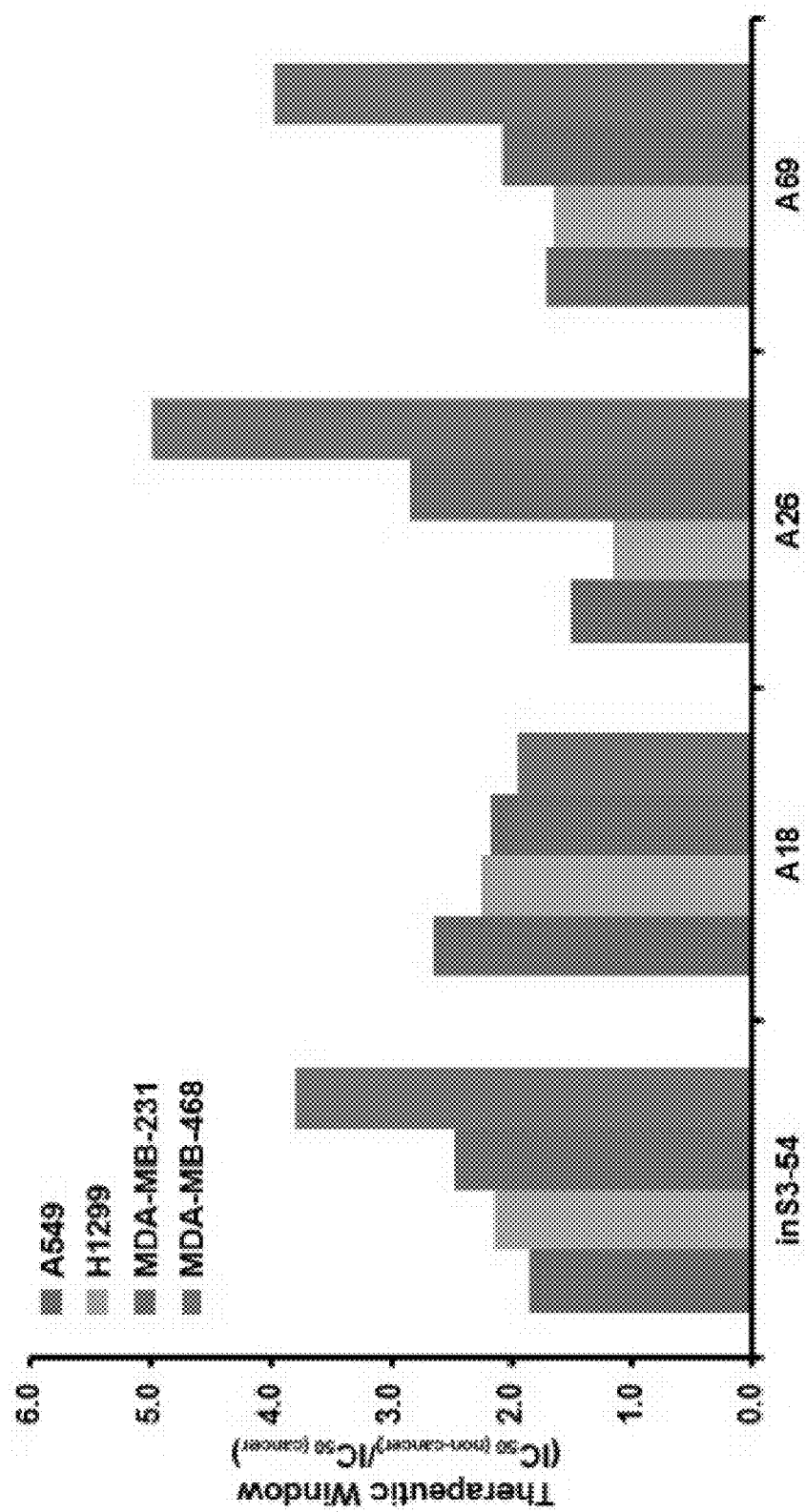
FIG. 17. In-vitro Therapeutic Window. The in-vitro therapeutic window is derived by dividing the $IC_{50}$ in non-cancerous cells by that in different cancer cells.

(FIG. 17). However, A26 appears to be toxic to noncancerous lung fibroblast with an $IC_{50}$ of 4.0 µM and a small in-vitro therapeutic window.

To determine if apoptosis contributes to analogue-induced loss of cancer cell viability, we performed ELISA analysis to determine and quantify cytoplasmic histone-associated DNA fragments that are released from apoptotic cells following treatment with A18 or A69 for 72 h. As shown in FIG. 16B, remarkable induction of apoptosis was observed in both lung and breast carcinoma cells following treatment by A18 or A69.

Selection of A18 as a Potential Lead for Further Investigation.

Based on above studies, it is clear that the parent compound inS3-54 is less specific to STAT3 than its analogues A18, A26, and A69 and, thus, was eliminated. A26 exerted high level cytotoxicity to lung fibroblast and was also eliminated. In acute in-vivo toxicity studies, A69 performed poorly and caused death of mice at 0.5 mg/kg. Furthermore, inS3-54, A26, and A69 all have poor solubility. On the other hand, A18 is completely soluble in a commercial oral formulation (Pharmatek Laboratories, San Diego, Calif.) for in-vivo studies. It has little cytotoxicity to noncancerous cells and can be tolerated by mice up to 200 mg/kg with multiple dosing. Thus, A18 was selected for further investigation.

A18 Inhibits Cancer Cell Migration and Invasion.

Figure 18:
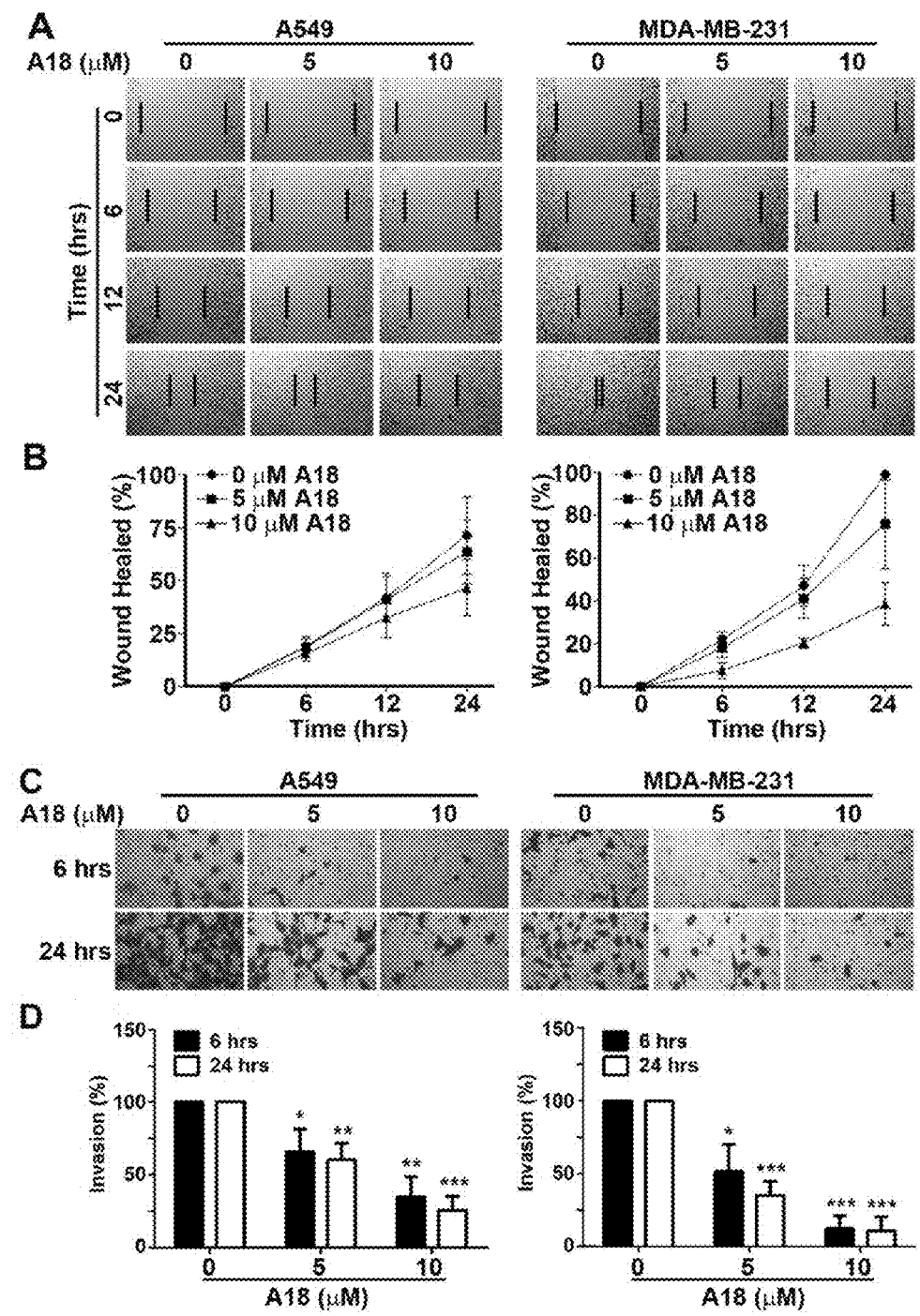
FIG. 18. A18 inhibits cancer cell migration and invasion. (A and B) Effect of A18 on migration. Panel B shows quantification analysis of wound healing assay from triplicate measurements of three independent experiments shown in panel A. (C and D) Effect of inS3-54 on cell invasion. Panel D shows quantification of invasion from measurement of 10 random views each of three independent experiments shown in panel C. (*p<0.05; p<0.01; *p<0.001).

To further characterize A18, we assessed the effects of A18 on cancer cell migration using wound-healing assay and invasion using Matrigel invasion assay. As shown in FIG. 18A, at 24 hours, 71% and 99% of wounds were healed in the absence of A18 for A549 and MDA-MB-231 cells, respectively. However, 64% and 76% of wounds were healed following 5 µM A18 treatment in A18 for A549 and MDA-MB-231 cells, respectively. A18 at 10 µM further reduced the healing to 47% and 39% for A549 and MDA-MB-231 cells, respectively.

Figure 19:
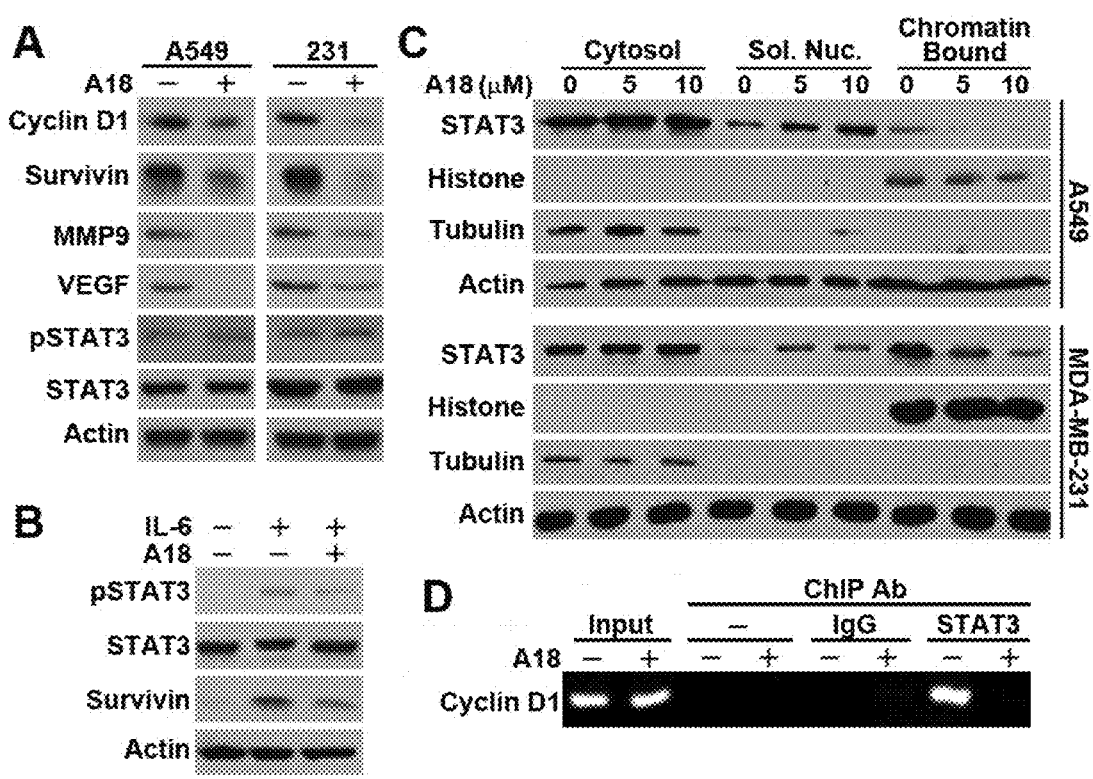
FIG. 19. A18 inhibits the expression of STAT3 downstream target genes and STAT3 binding to chromatin. (A) Effect of A18 on the expression of STAT3 downstream target genes in A549 and MDA-MB-231 cells. (B) A18 inhibition of IL-6 (25 ng/ml) stimulated STAT3 activation in serum-starved A549 cells. Actin was used as a loading control. (C and D) InS3-54 inhibition of STAT3 binding to chromatin in-situ as determined using subcellular fractionation and Western blot analysis (C) or ChIP assay of cyclin D1 promoter (D).

FIG. 18B shows that treatment with 5 µM A18 for 6 hours inhibited 66% and 51% of A549 and MDA-MB-231 cell invasion, respectively. Treatment with 10 µM A18 for 6 hours further reduced cell invasion to 35% and 13%, respectively. Treatment for 24 hours did not dramatically further reduce cell invasion. Although 100% confluent cells were used and the inhibition of invasion was observed at 6 hours of treatment, the potential of contribution to invasion inhibition by A18 inhibition of proliferation and induction of apoptosis cannot be ruled out. To test if this is the case, we analyzed cell proliferation and apoptosis under the same condition as wound-healing and Matrigel invasion assays following A18 treatment for 6 and 24 hours. FIG. 19 shows that treatment with 5 and 10 µM A18 for 6 or 24 hours has no significant effect on proliferation and apoptosis of confluent A549. Although A18 treatment for 24 hours reduced <20% proliferation of MDA-MB-231 cells, it did not induce any apoptosis. Under the same condition, much more inhibition of invasion was observed (FIG. 18B). Thus, A18 inhibition of cancer cell migration and invasion may not be due to its effect on apoptosis and cell proliferation.

A18 Inhibits the Expression of STAT3 Downstream Target Genes and the Binding of STAT3 to its Endogenous Target Sequences.

Figure 20:
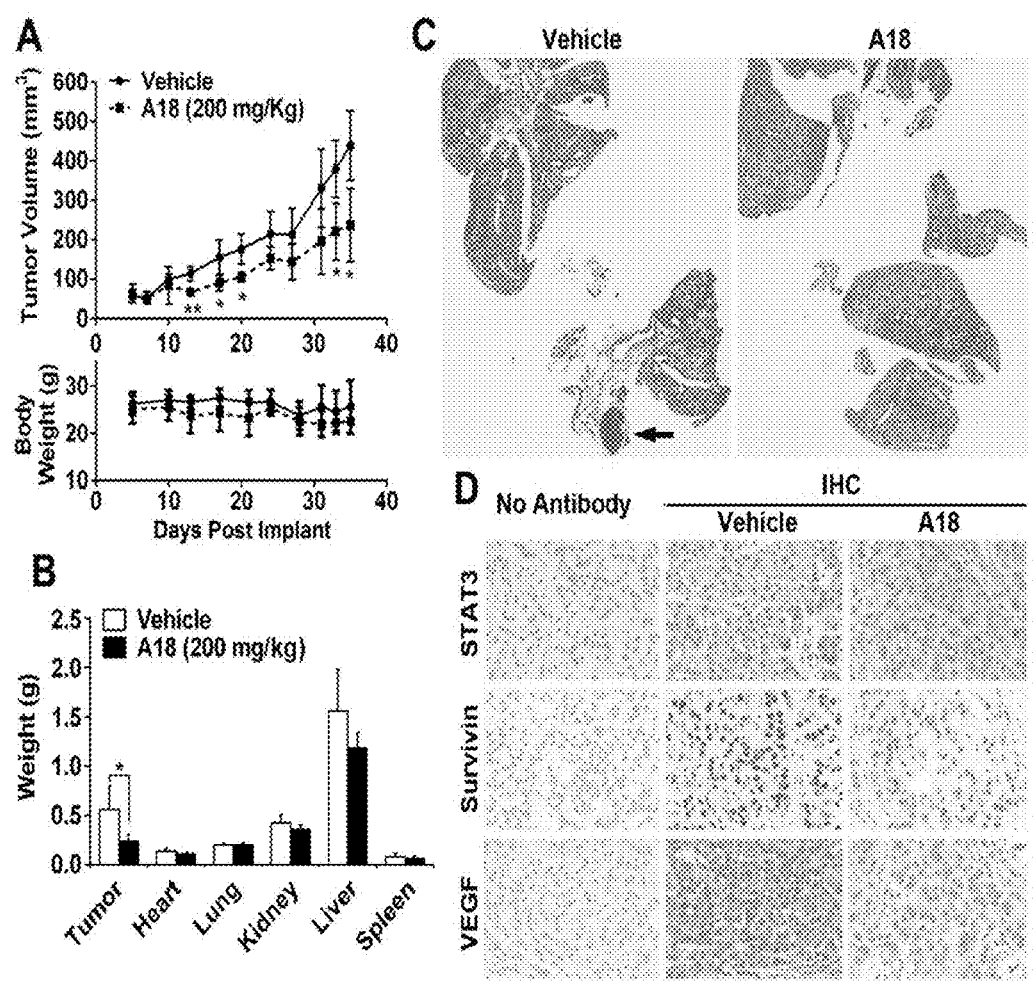
FIG. 20. A18 suppresses xenograft tumor growth in vivo. (A) Volume of xenograft tumors and body weight of mice following implantation. (B) Wet weight of final dissected xenograft tumor mass and organs. A single outlier in the treatment group was rejected by Dixon's Q test at 95% confidence. (C) H&E-stained paraffin sections of lung tissues of vehicle and A18-treated mice. The arrow indicates a solitary metastatic tumor. (D) Immunohistochemistry staining of xenograft tumor tissues using STAT3, survivin, and VEGF antibodies. (*p<0.05).

To investigate the potential effect of A18 on the expression of STAT3 downstream target genes and thereby validate its inhibitory effect on STAT3 in cells, we performed Western blot analysis of cyclin D1, survivin, MMP-9 and VEGF following A18 treatment of A549 and MDA-MB-231 cells. As shown in FIG. 20A, the expression of all these genes was decreased in both cell lines following A18 treatments.

To further determine the STAT3-inhibitory activity of A18, we tested if A18 can inhibit cytokine-induced STAT3 activation and expression of its downstream genes. For this purpose, A549 cells were serum starved and treated with DMSO vehicle or 10 µM A18 followed by IL-6 stimulation and Western blot analysis of phospho-STAT3 (Tyr705) and survivin. As shown in FIG. 20B, IL-6 induced activation of STAT3 and expression of survivin following serum starvation and A18 treatment did not inhibit IL-6-induced STAT3 activation. However, IL-6-induced survivin expression was inhibited by A18. These data, together with that shown in FIG. 20A, suggest that A18 does not affect the constitutive or IL-6-induced STAT3 expression but represses the expression of STAT3 target genes.

Figure 13:
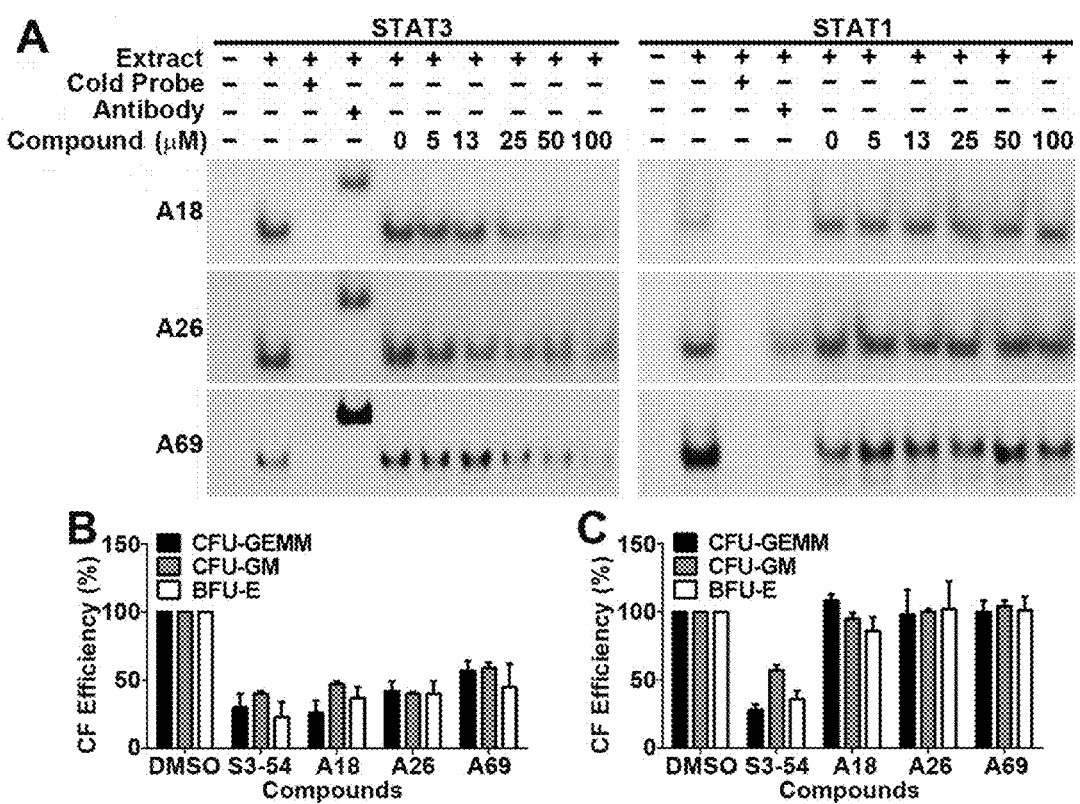
FIG. 13. STAT3 selectivity and specificity of active analogues A18, A26, and A69. (A) Effects of A18, A26, and A69 on in-vitro DNA binding activity of STAT3 and STAT1. Whole cell lysate of H1299 cells with transient expression of FLAG-STAT3 or STAT1 were pre-treated without or with excess cold probe, antibody, or different concentrations of active analogues A18, A26, and A69 followed by incubation with [$^{32}$P]-labeled probe and analysis on non-denaturing PAGE. (B-C) Effects of A18, A26, and A69 on colony formation of hematopoietic progenitor cells. Hematopoietic progenitor cells isolated from STAT3$^{+/-}$ (B) and STAT3$^{-/-}$ (C) mice were subjected to colony formation assay in the presence of DMSO control or 20 µM inSTAT3-54, A18, A26 or A69.

As shown in FIG. 13, A18 along with A26 and A69 all inhibited in-vitro DNA—binding activity of STAT3 using EMSA. To determine if A18 inhibits STAT3 binding to chromatin DNA in-situ, we treated A549 and MDA-MB-231 cells with A18 followed by fractionation and Western blot analysis of cytosolic, soluble nuclear and chromatin-bound STAT3. FIG. 20C shows that the chromatin-bound STAT3 decreases while soluble nuclear STAT3 increases with the increasing concentration of A18, suggesting that A18 effectively inhibits the binding of STAT3 to its target sequence on chromatin DNA in situ. To confirm this finding, we performed ChIP assay of STAT3-bound to the promoter of a STAT3 downstream target gene cyclin D1. As shown in FIG. 20D, A18 treatment eliminated STAT3 binding to the promoter of cyclin D1 gene. Thus, we conclude that A18 treatments inhibit STAT3 binding to the promoters of its target genes on chromatin in situ and inhibits the expression of these genes.

A18 Inhibits Tumor Growth and Metasatsis and Expression of STAT3 Target Genes In Vivo.

Figure 21:
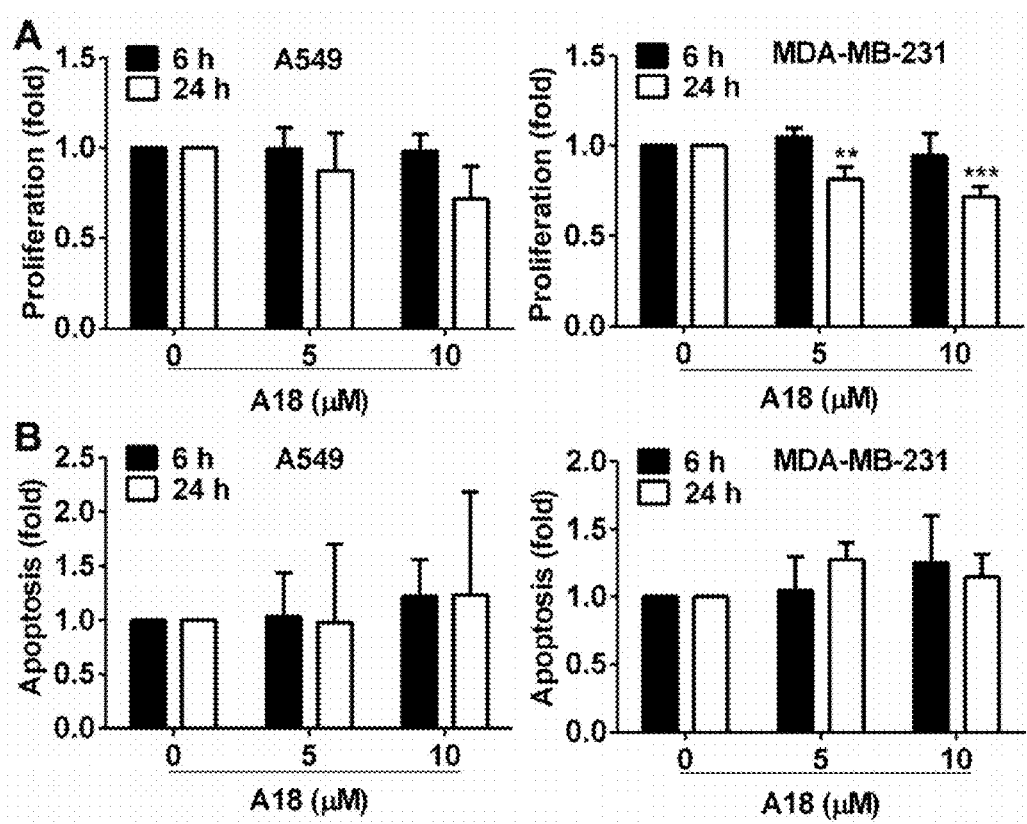
FIG. 21. Effects of inS3-54A18 on cell growth and apoptosis of confluent cells. 100% confluent A549 and MDA-MB-231 cells were treated with DMSO (1%0), 5 or 10 µM inS3-54A18 for 6 or 24 hrs followed by determination of change in cell number for proliferation (A) or ELISA for apoptosis (B). *p<0.05, **p<0.01, by Student's t-test as compared with control.

We next evaluated the in-vivo efficacy of A18 in a mouse xenograft model of A549 cells. As shown in FIG. 21A, A18 treatment significantly reduced tumor growth compared to the vehicle control treatment. However, it had no significant effect on mouse body weight. The final tumor weight in the A18-treated mice is significantly less than that of the control-treated group (FIG. 21B) while there are no difference in the weight of other organs. Following H&E staining and histology analysis, secondary metastatic tumors were found in the lungs of 3 mice in the control group with extension into the peripancreatic adipose tissues and the adjacent peripancreatic lymph nodes (FIG. 21C). None of the A18-treated mice has any signs of lung metastasis. Immunohistochemistry staining analysis of xenograft tumors also revealed that the expression of STAT3 downstream target genes, survivin and VEGF, but not STAT3 itself were reduced by A18 treatment compared to vehicle-control treatment. These findings suggest that A18 may be effective in suppressing xenograft tumor growth and metastasis with little adverse effect.

Discussion.

Here, we successfully identified a lead inhibitor, A18, targeting the DBD of STAT3. A18 not only binds to the DBD of STAT3, it also inhibits the DNA-binding activity of STAT3 both in vitro and in situ as well as the expression of STAT3 downstream target genes. It further suppressed xenograft tumor growth and metastasis possibly by inhibiting STAT3 activity in vivo. Interestingly, A18 is completely soluble in an oral formulation and is likely specific to STAT3. Furthermore, A18 is tolerable by mice up to 200 mg/kg in multiple dosing. These characteristics make A18 a promising potential lead inhibitor for further modification and development.

The DBD of transcription factors has been considered "undruggable" because disrupting protein-DNA interactions with small molecules targeting DNA-binding domains (DBDs) of transcription factors is very challenging due to potentially limited selectivity. The findings as described here on the analogues of inS3-54 designed targeting the DBD of STAT3 not only further validate that the improved in-silico screening approach of this invention is effective in identifying STAT3-selective inhibitors targeting DBD of STAT3, these findings challenges the prevailing dogma that the DBD of transcription factors is "undruggable" and show that targeting DBD is accomplishable with appropriate approaches.

Although a decoy oligonucleotide, which binds to DBD of STAT3, is currently in clinical trial on head and neck cancers as a biological drug it may have potential issues compared to a small molecule drug. Firstly, small molecule compounds are stable over time and rarely initiate immune responses. In contrast, oligonucleotides are less sable and can potentially trigger significant immune responses. Secondly, the inherent unstable nature of oligonucleotides requires special techniques during production, evaluation, transportation and storage which ultimately drive up the cost. Thus, identification of a lead small molecule inhibitor targeting the DBD of STAT3 may lead to a clinically useful, stable, and affordable anticancer drug targeting STAT3.

Figure 22:
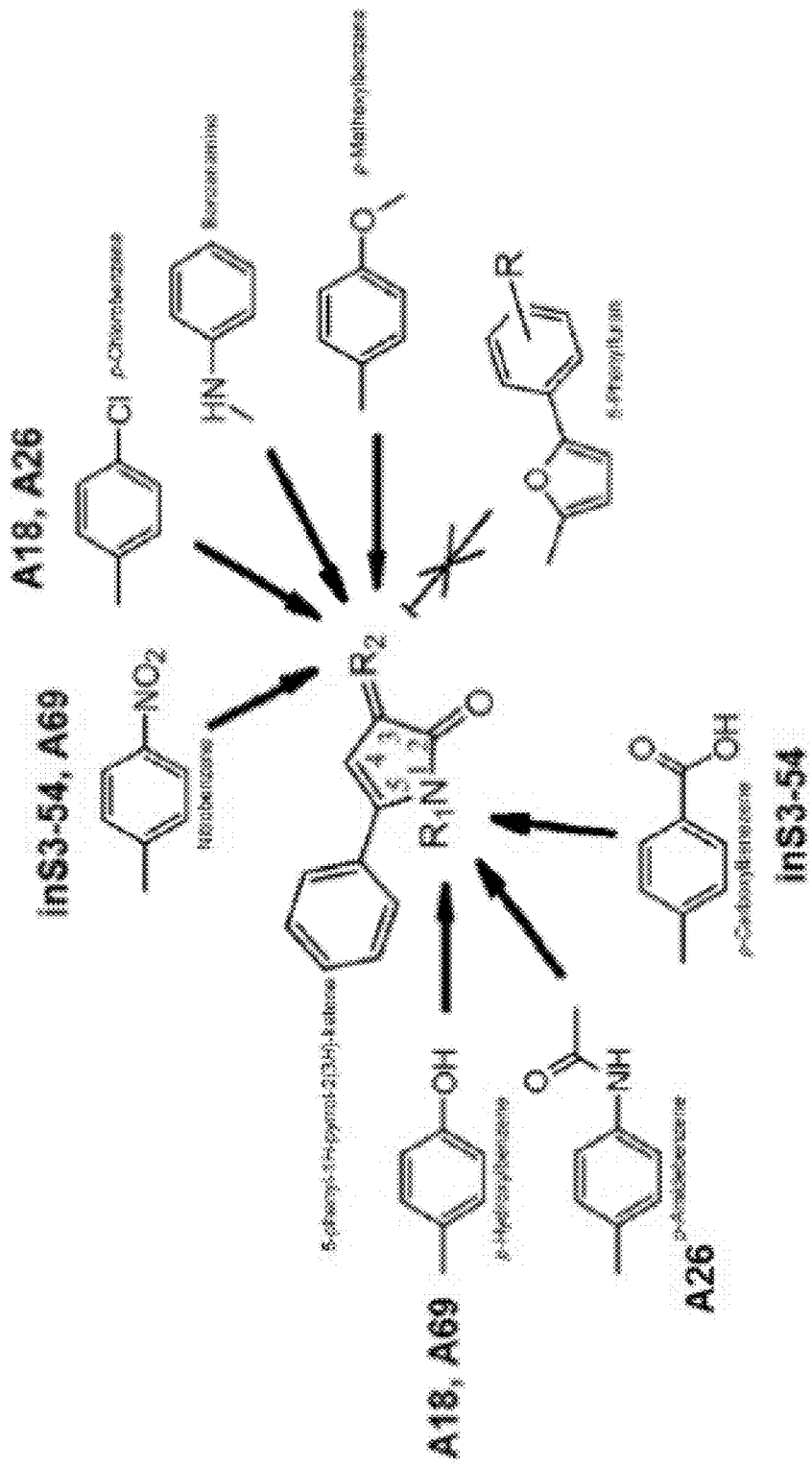
FIG. 22. Structure-Activity Relationship of active analogues of inS3-54. Most active analogues of inS3-54 contain a core structure, and the activity in inhibiting STAT3 depends on the different substituent groups at the R1 and R2 positions. For analogues A18, A26 and A69, these compounds show comparable activity in inhibiting STAT3 DNA binding activing and cell proliferation.

Analysis of inS3-54 analogues revealed the key structural determinants. First of all, inS3-54 and most of analogues contain a core structure of 5-phenyl-1H-pyrrol-2(3H)-ketone. Secondly, it appears that the activity of these compounds in inhibiting STAT3 varies based on the modification of the $R_1$ and $R_2$ side groups in the core structure. As shown in FIG. 22, the nitrobenzene at the $R_2$ position of inS3-54 contributes to the binding of the residues Met331, Val343, Met420, Ile467 and Met470 of STAT3 via hydrophobic interaction. The carboxyl group on the benzene ring at $R_1$ position stabilizes the binding via electrostatic interaction with the residues Lys340 and Asn466 of STAT3. However, the docking of inS3-54 onto STAT1 is unfavorable with physical hindrance. Therefore, both $R_1$ and $R_2$ groups may be critical for the activity and specificity of these compounds. A general review of inS3-54 analogues reveals that the STAT3 inhibitory activity of the compounds increased with the $R_2$ group being nitrobenzene, p-chlorobenzene, benzenamine and p-methoxylbenzene, but decreased with $R_2$ group being 5-phenylfuran. The $R_1$ group is also one of the important determinants of STAT3-inhibiting activity. The existence of p-hydroxyl, p-carboxyl and p-amide side groups on the benzene ring facilitated the activity of these compounds. However, this relationship is not absolute; the activity of the compounds is more likely to depend on the combination of $R_1$ and $R_2$ side groups in the core structure. All three active analogues of inS3-54 exhibited more potent or comparable activity on inhibition of STAT3-dependent signaling, DNA-binding activity, and cancer cell survival than the initial hit and all compounds are specific to STAT3 protein as demonstrated by the colony formation assay of STAT3$^{+/+}$ and STAT3$^{-/-}$ cells.

It is also noteworthy that the specificity of the three active inS3-54 analogues appears to be determined by the side group on 1-benzene ring at 4'-position. While the STAT3 specific inhibitors A18, A26 and A69 have hydroxyl or amide groups at this position, the non-specific inhibitor inS3-54 has carboxyl group. Replacing the hydroxyl or amide groups by carboxyl group at this position may abolish the specificity of these compounds to STAT3 and enable them to bind to other proteins. Besides, the combination of various R groups may affect the in vivo properties. For example, a pilot pharmacokinetic study revealed a very low plasma concentration of inS3-54 and A26 due to their poor solubility and absorption with much deposit in peritoneal cavity. A69 appears to work on STAT3 faster than other compounds with shortest time to achieve 50% inhibition on STAT3-dependent luciferase reporter (FIG. 14), but a pilot toxicity study reveals that the compound is toxic to mice with a tolerance dose of less than 0.5 mg/kg (data not shown). However, A18 has acceptable activity on STAT3 signaling and good solubility of up to 100 mg/mL in a commercial vehicle for animal studies. Eventually, A18 was chose as a lead.

Cell Lines.

Human cancer cell lines A549, MDA-MB-231, MDA-MB-468, and human lung fibroblast IMR90 were cultured in DMEM containing 10% FBS and appropriate antibiotics in a 5% $CO_2$ incubator at 37° C. H1299 cells were maintained in RPMI 1640 medium containing 10% FBS and appropriate antibiotics. Human mammary epithelial cell line MCF10A1 was cultured in DMEM/F-12 (50:50) with 10% equine serum, 10 µg/mL insulin, 25 ng/mL epidermal growth factor, 500 ng/mL hydrocortisone, and 100 ng/mL cholera toxin.

Hematopoietic Progenitor Cell Colony Formation Assay.

Hematopoietic progenitor cell colony formation assay was performed as previously described. Briefly, $5 \times 10^4$ STAT3$^{+/+}$ and STAT3$^{-/-}$ mouse (C57BL/6) bone marrow cells were stimulated in vitro with 1 U/ml recombinant human erythropoietin, 50 ng/ml recombinant mouse stem cell factor and 5% vol/vol pokeweed mitogen mouse spleen cell conditioned medium, and 0.1 mM hemin in the presence of either IMDM medium, IMDM medium plus inS3-54 analogues or DMSO vehicle control. Colonies were scored seven days after incubation at 37° C. with 5% $CO_2$ and lowered (5%) $O_2$.

DNA-Binding Activity Assays.

EMSA (electrophoretic mobility shift assay) was used for testing in-vitro DNA-binding activity of STAT3 as previously described, Briefly, 20 µg lysate of H1299 cells with transient expression of FLAG-tagged STAT3c or STAT1 was pre-incubated with compounds or vehicle, specific antibodies to STAT3 or STAT1 (Santa Cruz), or excess cold SIE probe (5'-AGCTTCATTTCCCGTAAATCCCTA-3' SEQ ID NO: 2) for 30 mins at room temperature in binding buffer (0.1 µg/µL poly(dI·dC), 10 mM HEPES·KOH, pH 7.9, 50 mM KCl, 10% glycerol, 0.05 µg/µL BSA, 1 mM DTT and 0.2 mM PMSF) before incubating with $4 \times 10^4$ cpm [$^{32}$P]-labeled SIE probe for 20 min at room temperature. The reactions were separated on 6% non-denaturing polyacrylamide gel signals were detected by autoradiography.

The in-situ DNA-binding activity of STAT3 was performed by analyzing chromatin-bound STAT3 also as previously described. Briefly, following treatment with compounds or DMSO vehicle control, cells were harvested and subjected to subcellular fractionation to separate cytotosol, soluble nuclear, and chromatin-bound proteins followed by Western blot analysis of STAT3 in these fractions.

Conjugation of A26 and Pull-Down Assay.

A26 containing an imino group was immobilized to CNBr-activated Sepharose 4B (GE Healthcare, Uppsala, Sweden) according to manufacturer's instruction. Vehicle-treated and an inactive compound PhP-conjugated CNBr-activated Sepharose 4B were also generated in the same way as control beads. Since A26 is yellow in color, conjugation of A26 to CNBr-activated Sepharose 4B was verified by monitoring the change in color of the beads. For pull-down assay, A26-conjugated and control beads equilibrated with binding buffer (20 mM Tris-HCl, pH 8.0, 150 mM KCl, 1 mM EDTA, 15% glycerol, 0.5% NP-40) were blocked with 10% milk in the binding buffer containing 0.2 mM PMSF and 1:1000 diluted protease inhibitor cocktail (Sigma-Aldrich, St. Louis, Mo.) followed by incubation with 120 µg total lysate of H1299 cells with FLAG-STAT3c in the same buffer at 37° C. for 1 hr. Unbound proteins were removed by washing beads 7 times with the binding buffer and the bound proteins were separated by SDS-PAGE followed by analysis of FLAG-STAT3 using Western blot. For competition analysis, cell lysate was pre-incubated with DMSO vehicle or different compound for 1 hour at 37° C. prior to pull down assay using A26-conjugated beads.

Survival, Apoptosis, Migration, and Invasion Assays.

Survival, apoptosis, migration, and invasion assays were performed as previously described. Briefly, effect of STAT3 inhibitors on cell survival were analyzed using sulforhodamine B (SRB) assay. Apoptosis induced by STAT3 inhibitors cells were quantified using Cell Death Detection ELISA$^{PLUS}$ Kit (Roche, Mannheim, Germany) by enzyme-linked immunosorbent assay (ELISA) according to manufacturer's instructions. Wound filling assay was performed by culturing $1\times10^5$ cells/well in 6-well plates, followed by generating a wound using a pipet tip and continuous culture with photographic recording at different times. Cell invasion assay was performed using Matrigel-coated Boyden Chambers (BD Biosciences, Bedford, Mass.) following manufacturer's instructions with $1.25\times10^5$ cells/well.

Chromatin Immunoprecipitation (ChIP).

ChIP was performed as previously described. Briefly, H1299 cells were treated with 1% formaldehyde for 10 min and lysates of the cells were sonicated to shear DNA to lengths between 200 and 1000 bases, which were then subjected to ChIP using Chromatin Immunoprecipitation Assay Kit (EMD Millipore, Billerica, Mass.) and normal IgG or STAT3 specific antibody (Santa Cruz) according to manufacturer's instructions. The primers for PCR of cyclin D1 promoter are 5'-AACTTGCACAGGGGTTGTGT-3' SEQ ID NO: 23 (forward) and 5'-GAGACCACGAGAAGGGGT-GACTG-3' SED ID NO: 24 (reverse).

Efficacy Analysis Using Xenograft Mouse Model.

For efficacy study. $5\times10^6$ A549 cells were injected subcutaneously in the flanks of 12 NOD/SCID mice. When the tumor volume reached about 50.0 mm$^3$, the mice were randomized into two different groups (6/group) with one treated by formulation vehicle control (Pharmatek Laboratories, San Diego, Calif.) and the other by A18 at 200 mg/kg with oral dosing every two days for four weeks. One mouse in each group died during the study and was eliminated. Tumor volume and body weight were measured twice a week. On the 35$^{th}$ day after implant, mice were euthanized and the tumor tissues were harvested and weighed. Necropsy was also performed to determine the changes in heart, lungs, kidneys, liver and spleen. To evaluate the histological alternation, metastasis in the lung and the expression of STAT3 and its downstream proteins, paraffin-embedded tissue sections were stained with ematoxylin and eosin (H&E) and/or used for immunohistochemistry analysis.

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

Bromberg et al. Oncogene. 2000; 19:2468-73.
Debnath et al. J Med Chem. 2012; 55:6645-68.
Lee et al. Current topics in microbiology and immunology. 2011; 344:41-59.
Chen et al. Medicinal research reviews. 2008; 28:185-200.
Devarajan et al. Current Mol. Med. 2009; 9:626-33.
Hirano T et al. Oncogene. 2000; 19:2548-56.
Dolled-Filhart et al. Cancer Research. 2003; 9:594-600.
Choi et al. J. Obstetrics and Gyn. Res. 2010; 36:304-10.
Diaz et al. Cancer Research. 2006; 12:20-8.
Yue et al. Expert Opin Investig Drugs. 2009; 18:45-56.
Deng et al. Curr Cancer Drug Targets. 2007; 7:91-107.
Ren et al. Bioorg Med Chem Lett. 2003; 13:633-6.
Turkson et al. J Biol Chem. 2001; 276:45443-55.
Turkson et al. Mol Cancer Ther. 2004; 3:261-9.
Siddiquee et al. ACS Chem Biol. 2007; 2:787-98.
Schust et al. Anal Biochem. 2004; 330:114-8.
Schust et al. Chem Biol. 2006; 13:1235-42.
Song et al. Proc Natl Acad Sci USA. 2005; 102:4700-5.
Siddiquee et al. Proc Natl Acad Sci USA. 2007; 104:7391-6.
Hao et al. Bioorg Med Chem Lett. 2008; 18:4988-92.
Fletcher et al. Chembiochem. 2009; 10:1959-64.
Lin et al. Neoplasia. 2010; 12:39-50.
Lin L et al. Cancer Res. 2010; 70:2445-54.
Yang et al. Genes Dev. 2007; 21:1396-408.
Timofeeva et al. J Biol Chem. 2012; 287:14192-200.
Nkansah et al. FEBS Lett. 2013; 587:833-9.
Caboni L, Lloyd D G. Medicinal research reviews. 2013; 33:1081-118.
Leung et al. Med Res Rev. 2013; 33:823-46.
Berg T. Curr Opin Chem Biol. 2008; 12:464-71.
Sen et al. Cancer Discov. 2012; 2:694-705.
Huang et al. ACS Chem Biol. 2014; 9:1063-214.
Welte et al. Proc Natl Acad Sci USA. 2003; 100:1879-84.
Mantel et al. Blood. 2012; 120:2589-99.
Huang et al. ACS Chem Biol. 2014; 9:1188-96.
Caboni L, Lloyd D G. Med Res Rev. 2012; 33:1081-118.
Brady et al. 2012; 63:257-77.
Hughes et al. Brit J Pharmacol. 2011; 162:1239-49. 1.
Darnell et al. *Science* 264, 1415-1421.
Zhong et al. *Science* 264, 95-98.
Bowman et al. *Oncogene* 19, 2474-2488.
Song, et al. *Oncogene* 22, 4150-4165.
Garcia et al. *Cell Growth Differ* 8, 1267-1276.
Bromberg, et al. *Cell* 98, 295-303.
Li et al. *Cancer Res* 67, 8494-8503.
Chiarle et al. *Nat Med* 11, 623-629.
Costantino et al. *Curr Med Chem* 15, 834-843.
Yue et al. *Expert Opin Investig Drugs* 18, 45-56.
Debnath et al. *J Med Chem* 55, 6645-6668.
Deng et al. *Curr Cancer Drug Targets* 7, 91-107.
Ren et al. *Bioorg Med Chem Lett* 13, 633-636.
Turkson et al. *Mol Cancer Ther* 3, 261-269.
Siddiquee et al. (2007) *ACS Chem Riot* 2, 787-798.
Schust, et al. (2004) *Anal Biochem* 330, 114-118.
Schust et al. (2006) *Chem Biol* 13, 1235-1242.
Song et al. (2005) *Proc Natl Acad Sci USA* 102, 4700-4705.
Siddiquee et al. (2007) *Proc Natl Acad Sci USA* 104, 7391-7396.
Zhang et al. (2012) *Proc Natl Acad Sci USA* 109, 9623-9628.
Yang et al. (2007) *Genes Dev* 21, 1396-1408.

Timofeeva et al. (2012) *J Biol Chem* 287, 14192-14200.
Nkansah et al. (2013) *FEBS Lett* 587, 833-839.
Caboni et al. (2012) *Med Res Rev* 33, 1081-1118.
Leung et al. (2013) *Med Res Rev* 33, 823-846.
Liu et al. (2005) *Nucleic Acids Res* 33, 3763-3771.
Frye, S. V. (2010) *Nat Chem Biol* 6, 159-161.
Buettner et al. (2011) *ACS Chem Biol* 6, 432-443.
Sehgal et al. (1998) *Am J Pathol* 152, 591-596.
Wei et al. (2003) *Oncogene* 22, 319-329.
Xie et al. (2004) *Oncogene* 23, 3550-3560.
Itoh et al. (2006) *Oncogene* 25, 1195-1204.
Cheng et al. (2008) *J Biol Chem* 283, 14665-14673.
Zhang et al. (2009) *Anticancer Res* 29, 4497-4501.
Pettersen et al. (2004) *J Comput Chem* 25, 1605-1612.
Lang et al. (2009) *RNA* 15, 1219-1230.
Meng et al. (1992) *J. of Computational Chemistry* 13, 505-524.
Graves et al. (2008) *J Mol Biol* 377, 914-934.
Onufriev et al. (2000) *Phys Chem B* 104, 3712-3720.
Liu et al. (2011) *J Chem Inf Model* 51, 2612-2625.
Liu et al. (2008) *Mol Cancer Ther* 7, 263-270.
Mendez et al. (2000) *Mol Cell Biol* 20, 8602-8612.
Liu et al. (2005) *Mol Pharmacol* 68, 430-438.

---

I claim:

1. A method of treating cancer, the method comprising the step of administering a therapeutically effective amount of a composition to a subject in need thereof, wherein the cancer is treated, and wherein the composition comprises:

(a) a pharmaceutically effective amount of an inhibitor of signal transducer and activator of transcription 3 (STAT3), or its pharmaceutically acceptable salt or a solvate thereof, wherein the inhibitor comprises the structure

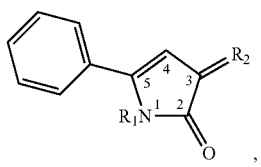

wherein R1 is selected from the group consisting of

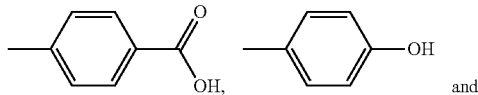

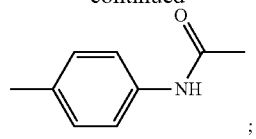

and wherein R2 is selected from the group consisting of

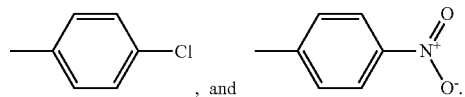

and (b) a pharmaceutically suitable carrier.

2. The method of claim 1, wherein the cancer is selected from the group consisting of breast and lung cancer.

3. The method of claim 1, wherein the inhibitor is formulated in an oral, topical, transdermal, parenteral, injection or infusion dosage form.

4. The method of claim 1, wherein the therapeutically effective amount ranges from about 0.001 µg/day to about 5 µg/day per kg bodyweight.

* * * * *